(12) United States Patent
Bierlmaier et al.

(10) Patent No.: US 9,718,810 B2
(45) Date of Patent: Aug. 1, 2017

(54) SOLID STATE FORMS OF A QUINAZOLINE DERIVATIVE AND ITS USE AS A BRAF INHIBITOR

(71) Applicant: Ignyta, Inc., San Diego, CA (US)

(72) Inventors: Stephen J. Bierlmaier, Thorndale, PA (US); Ralph C. Haltiwanger, West Chester, PA (US); Martin J. Jacobs, Versailles, KY (US)

(73) Assignee: IGNYTA, INC., San Diego, CA (US)

( * ) Notice: Subject to any disclaimer, the term of this patent is extended or adjusted under 35 U.S.C. 154(b) by 0 days.

(21) Appl. No.: 15/137,922

(22) Filed: Apr. 25, 2016

(65) Prior Publication Data

US 2016/0280698 A1 Sep. 29, 2016

Related U.S. Application Data

(63) Continuation of application No. 14/746,666, filed on Jun. 22, 2015, now Pat. No. 9,353,097, which is a continuation of application No. PCT/US2014/023110, filed on Mar. 11, 2014.

(60) Provisional application No. 61/776,081, filed on Mar. 11, 2013.

(51) Int. Cl.
| | |
|---|---|
| *C07D 413/12* | (2006.01) |
| *A61K 31/517* | (2006.01) |
| *C07D 239/88* | (2006.01) |
| *A61K 9/20* | (2006.01) |
| *A61K 9/48* | (2006.01) |
| *C07C 55/08* | (2006.01) |

(52) U.S. Cl.
CPC .............. *C07D 413/12* (2013.01); *A61K 9/20* (2013.01); *A61K 9/48* (2013.01); *A61K 31/517* (2013.01); *C07C 55/08* (2013.01); *C07D 239/88* (2013.01); *C07B 2200/13* (2013.01)

(58) Field of Classification Search
CPC ... C07D 413/12; C07D 239/88; A61K 31/517
USPC ........................................ 544/287; 514/266.2
See application file for complete search history.

(56) References Cited

U.S. PATENT DOCUMENTS

| | | | |
|---|---|---|---|
| 8,618,289 B2 | 12/2013 | Abraham et al. | |
| 8,969,587 B2 | 3/2015 | Abraham et al. | |
| 9,320,739 B2 | 4/2016 | Abraham et al. | |
| 9,353,097 B2 | 5/2016 | Bierlmaier et al. | |
| 2007/0244120 A1 | 10/2007 | Dumas et al. | |
| 2016/0199375 A1 | 7/2016 | Abraham et al. | |

FOREIGN PATENT DOCUMENTS

| | | |
|---|---|---|
| WO | WO 2009/117080 | 9/2009 |
| WO | WO 2012/138783 | 10/2012 |

OTHER PUBLICATIONS

Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Gura et al., Systems for identifying new drugs are often faulty, Science, 278:1041-1042, 1997.*
Adeyeye, Moji, ed., Preformulation in Solid Dosage Form Development (Informa Healthcare, 2008) Chapter 2.3, pp. 63-80.
Bastin et al., Organic Process Research & Development 2000, 4,427-435.
Gould, International J. of Therapeutics 33, pp. 201-213 & 217 (1986).
James et al., 2012, CEP-32496: a novel orally active BRAFV600E inhibitor with selective cellular and in vivo antitumor activity, Molecular Cancer Therapeutics, 11(4):930-941.
Liu, Rong, ed., Water-insoluble Drug Formulation: Pharmaceutical Salts, Chaper 15, pp. 417-435, (2008).
Morris, et al., International Journal of Pharmaceutics 105 (1994) 209-217.
Rowbottom et al., Identification of 1-(3-(6,7-Dimethoxyquinazolin-4-yloxy)phenyl)-3-(5-(1,1,1-trifluoro-2-methylpropan-2-yl)isoxazol-3-yl)urea Hydrochloride (CEP-32496), a Highly Potent and Orally Efficacious Inhibitor of V-RAF Murine Sarcoma Viral Oncogene Homologue B1 (BRAF) V600E, J Med Chem., 55, pp. 1082-1105 (published: Dec. 14, 2011).
Serajuddin, Advanced Drug Delivery Reviews 59 (2007) 603-616.
Stahl et al. eds., Handbook of pharmaceutical salts. Properties, selection and use (Wiley-VCH, 2008), pp. 265-327.
Swarbrick et al., eds. Encyclopedia of Pharmaceutical Technology 13 (Marcel Dekker, NY 1996) pp. 453-499.
International Search Report and Written Opinion dated Oct. 15, 2014 in PCT/US14/023110.
Organic Compound Crystal Preparation Handbook—Theory and Know-how-, Maruzen Co., Ltd., Jul. 25, 2008, pp. 57-84.
Takata, Drug Form Screening and Selection at Drug Development Stage, Pharm Stage, Jan. 15, 2007, vol. 6, No. 10, pp. 20-25.
Wermuth, New Drug-Creating Chemistry, Last Volume, Technomic Publishing Co., Inc., 1999 347-365.

\* cited by examiner

*Primary Examiner* — Deepak Rao

(74) *Attorney, Agent, or Firm* — Foley & Lardner LLP

(57) ABSTRACT

This application relates to various salts and solid state forms of Compound (I). This application also relates to pharmaceutical compositions and therapeutic uses of these materials and compositions.

15 Claims, 34 Drawing Sheets

Figure 2: Variable Temperature XRPD Patterns of Form A₀ (25°C - 225°C)

Figure 3: Overlay of DSC and TGA Curves of Form A₀

Figure 4: Gravimetric Vapor Sorption Isotherm of Form $A_0$

Figure 5: XRPD Patterns of Form A$_0$ before and after Gravimetric Vapor Sorption Analysis Figure 6: Infrared Spectra of Form $A_0$ Figure 7: Photograph of Form A₀ at Room Temperature FIG.8  XRPD Pattern of Bromide Form $A_1$ FIG. 10  GVS Isotherm of Bromide Form A₁

Figure 11: Kinetic Data/Mass Plot of Bromide Form A$_1$

Figure 12: XRPD Patterns of Bromide Form A₁ before and after GVS Analysis

Figure 14: Photograph of Bromide Form A₁ at Room Temperature
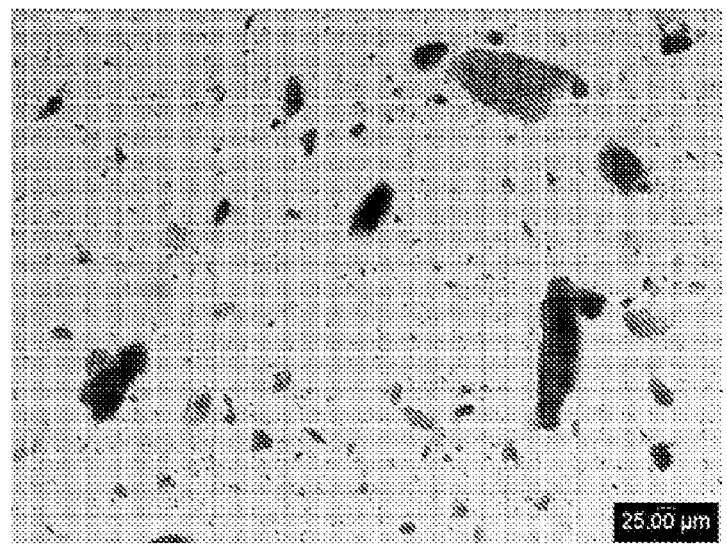

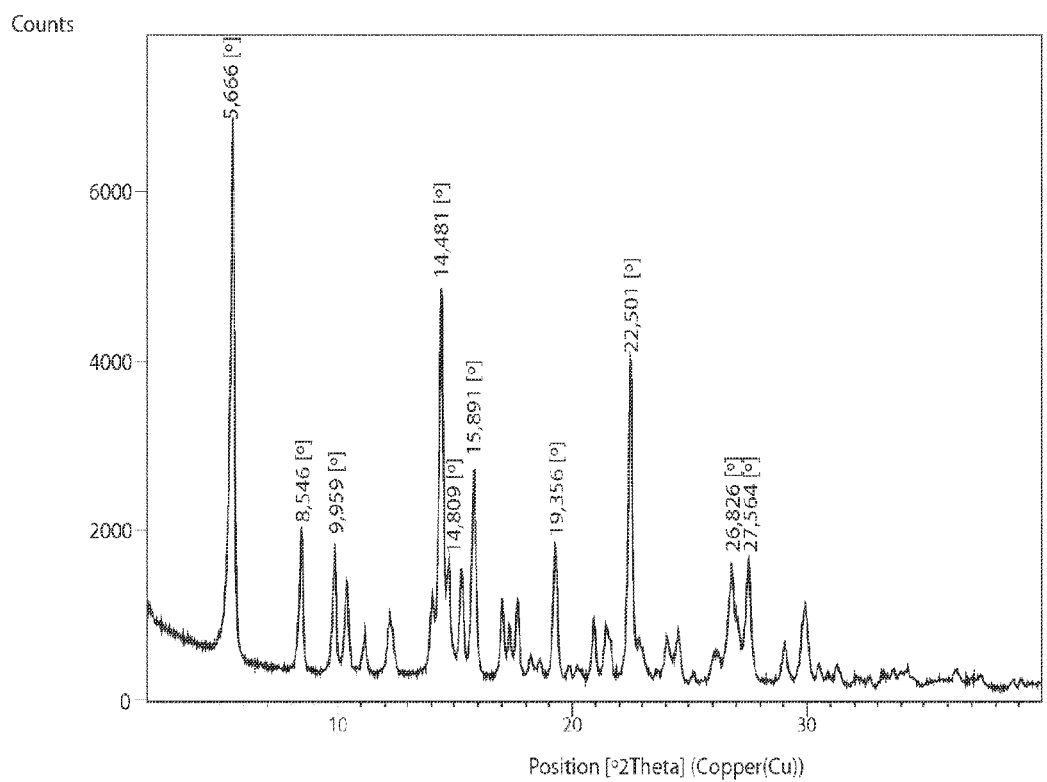
FIG. 15  XRPD Pattern of Chloride Form A₁

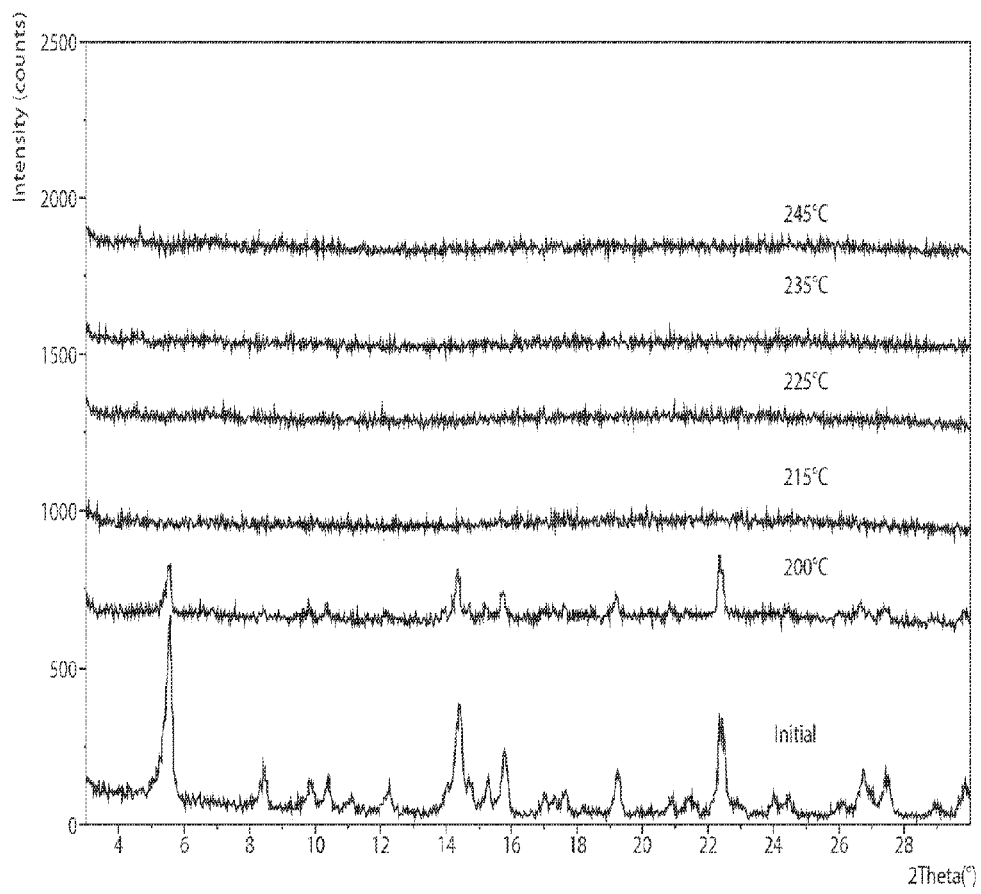

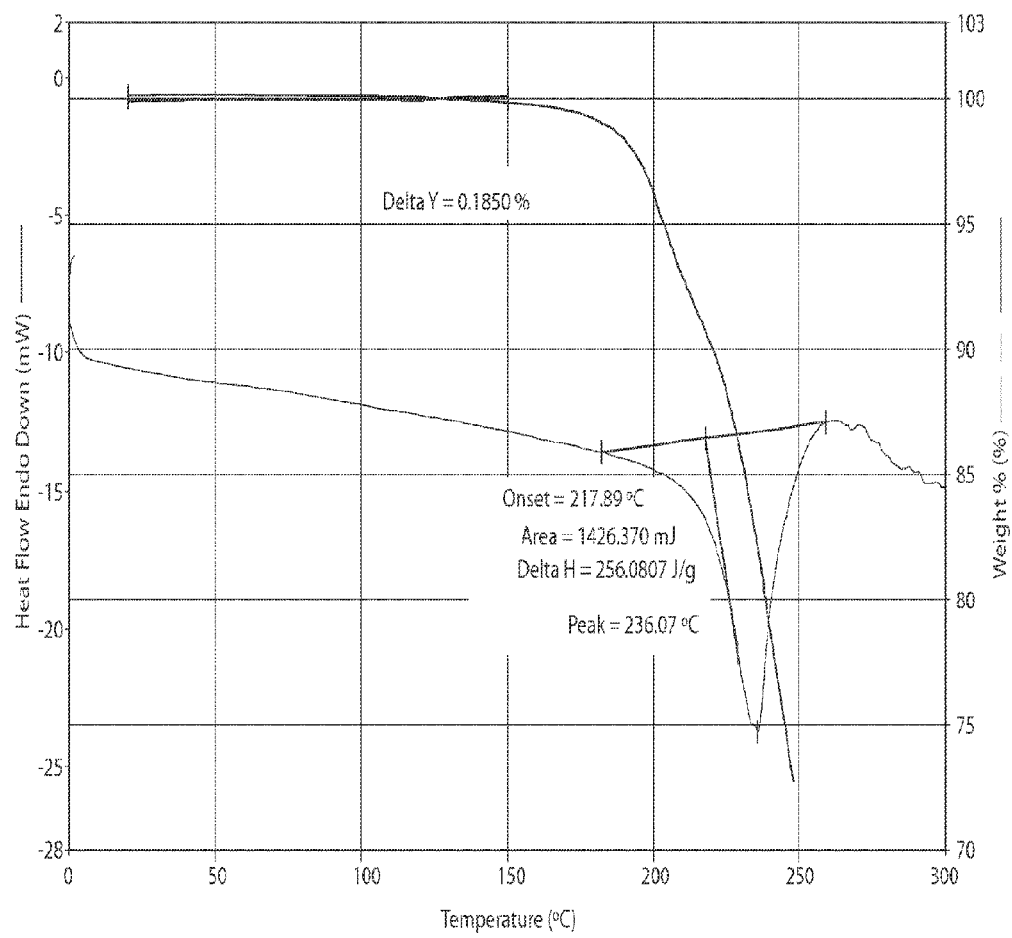

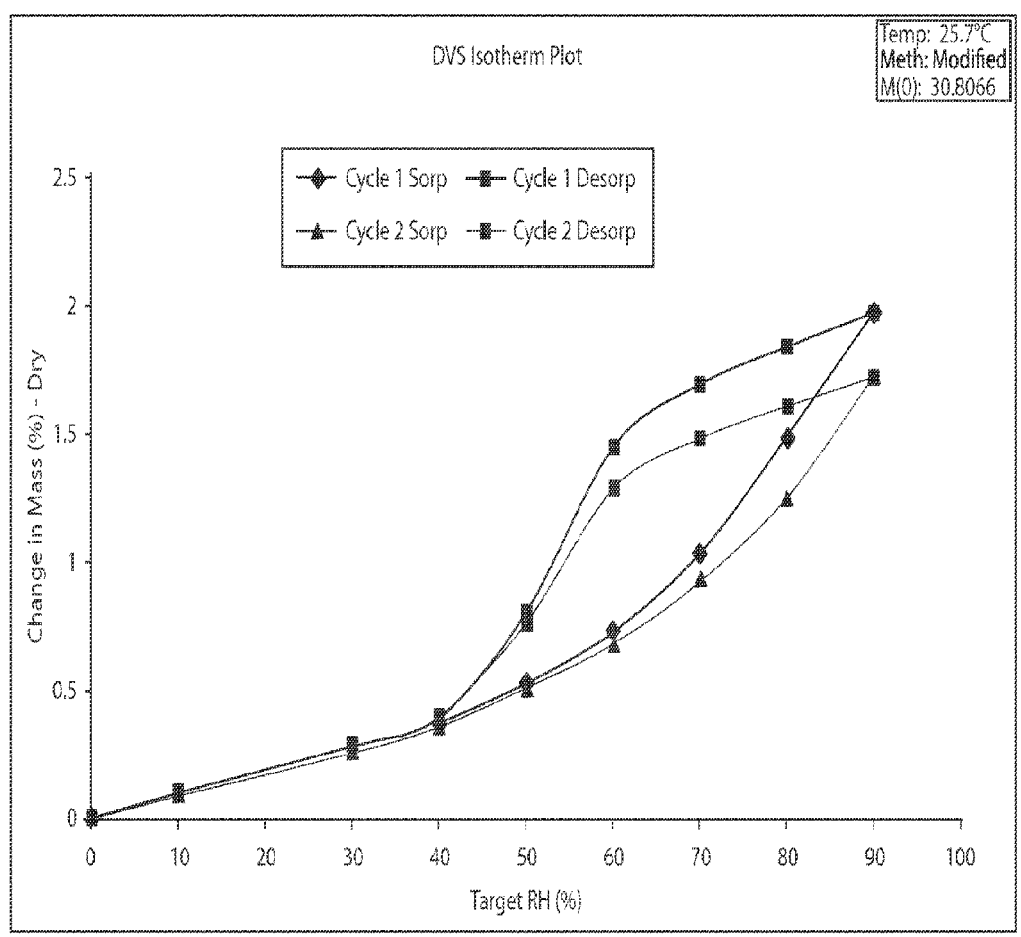
FIG.18  GVS Isotherm of Chloride Form A₁

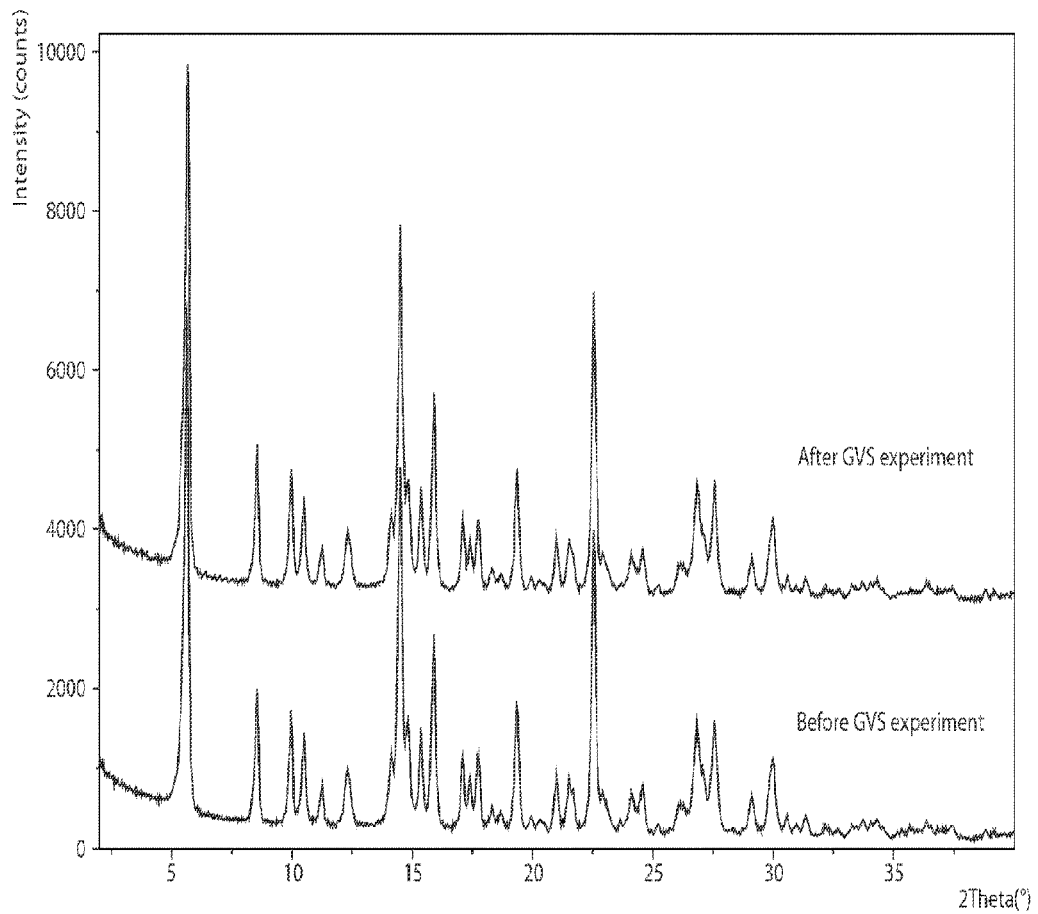

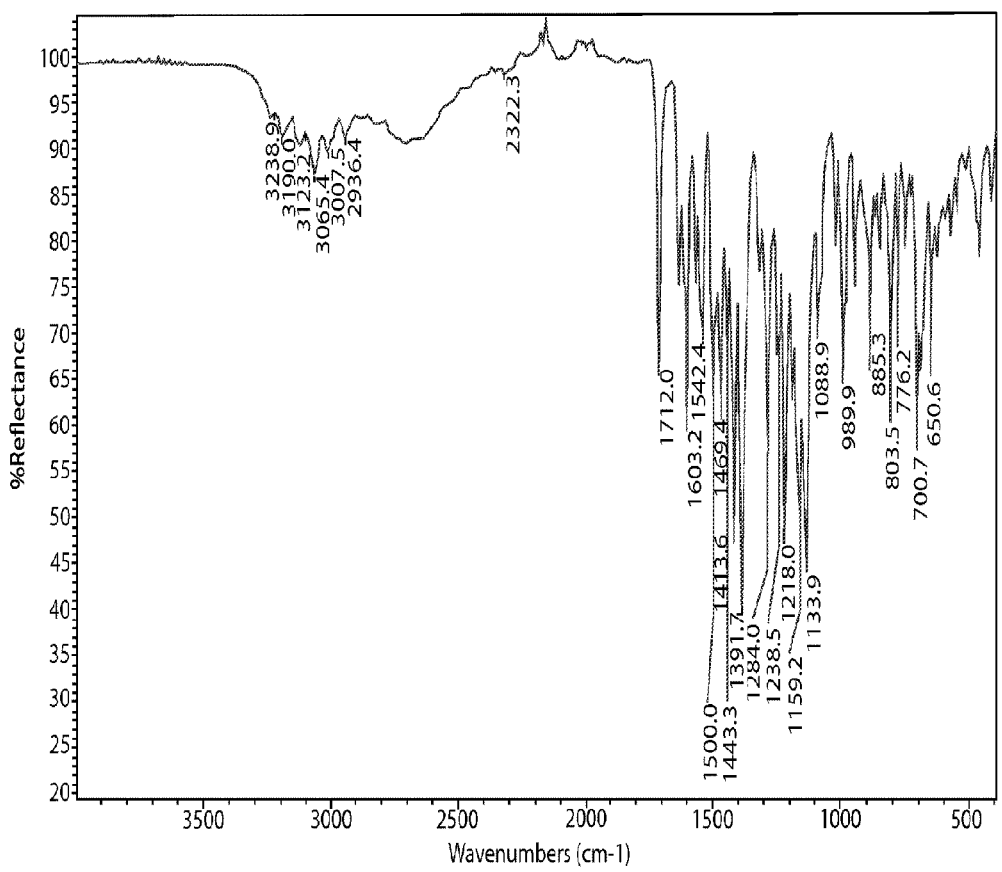
FIG.20 FTIR Spectrum of Chloride Form A₁

Figure 21: Photograph of Chloride Form A₁ at Room Temperature
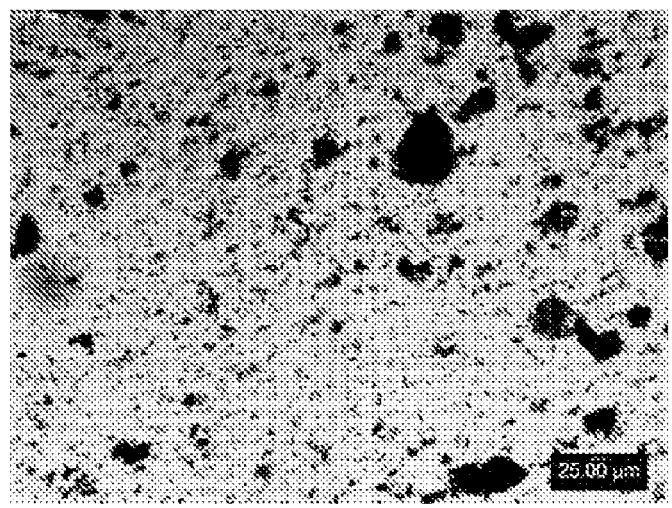

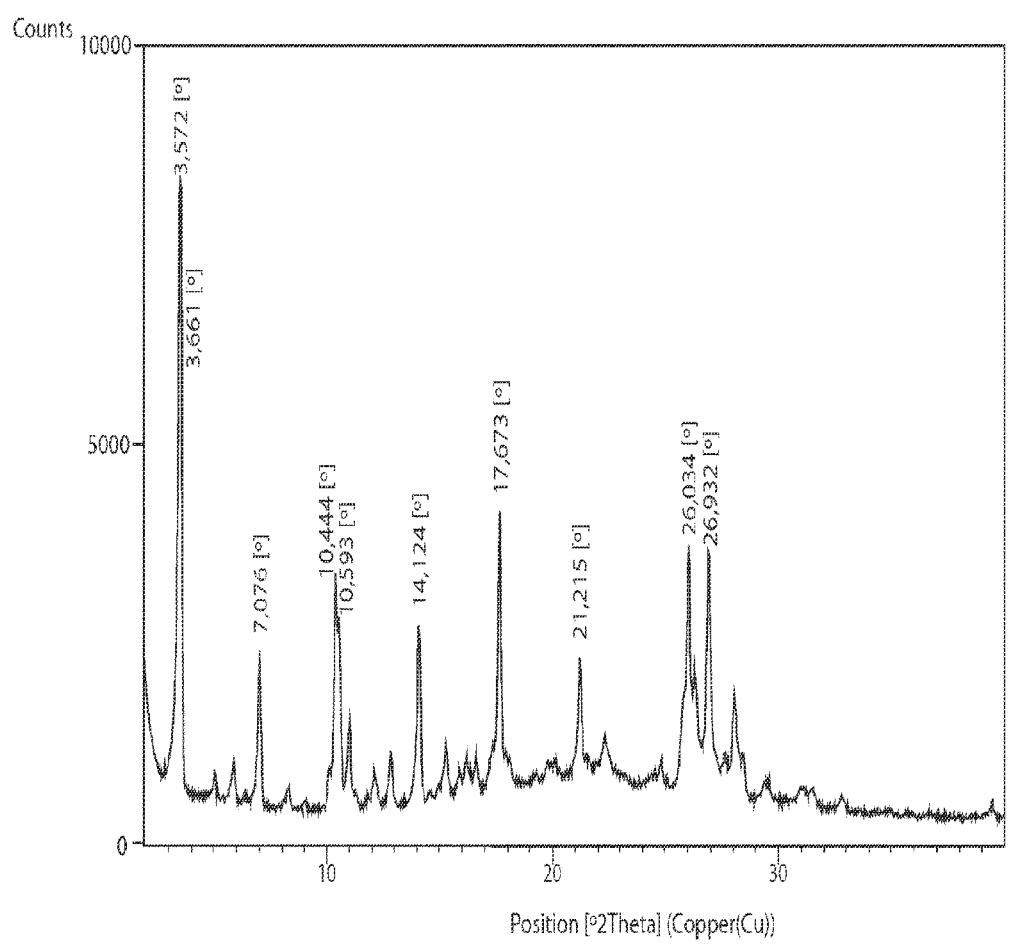
FIG.22 XRPD Pattern of Malonate Form A₁

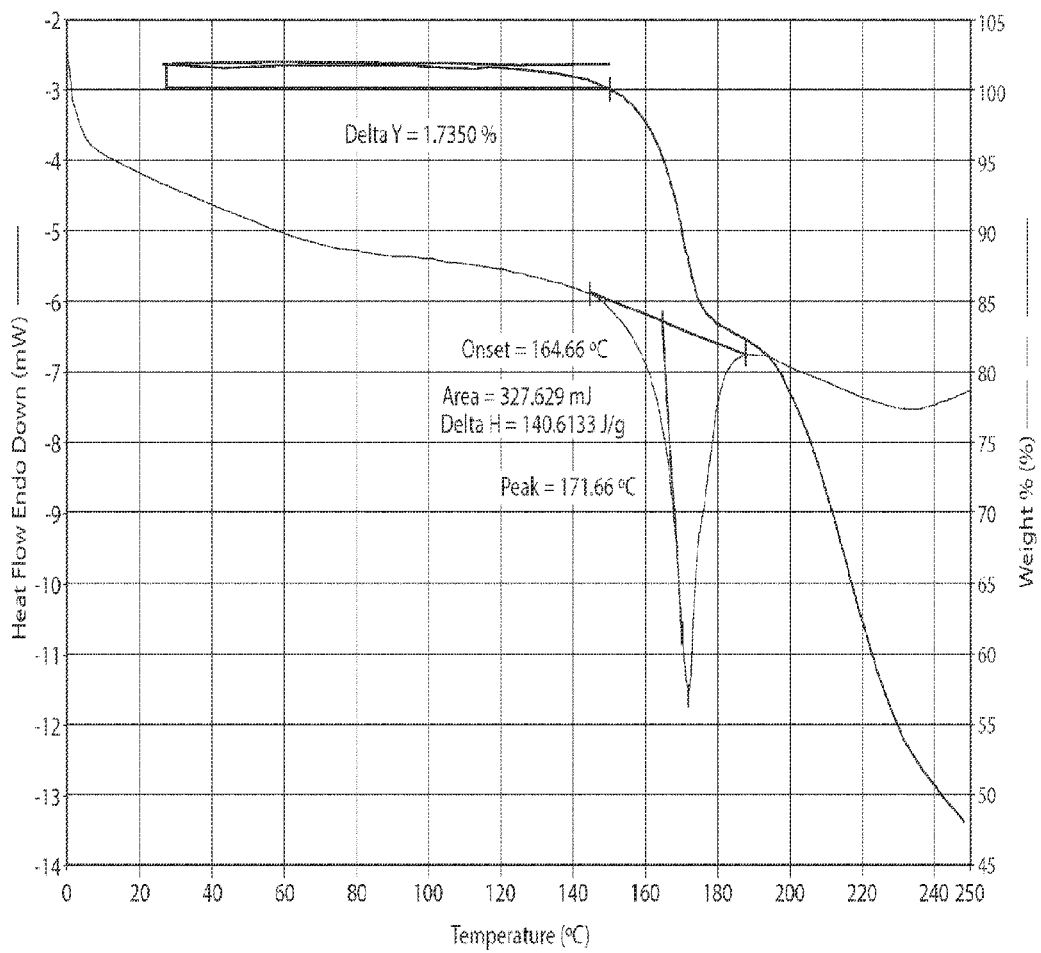
Figure 23A: Overlay of DSC and TGA Curves of Malonate Form $A_1$

Figure 23B: GVS Isotherm of Malonate Form A$_1$
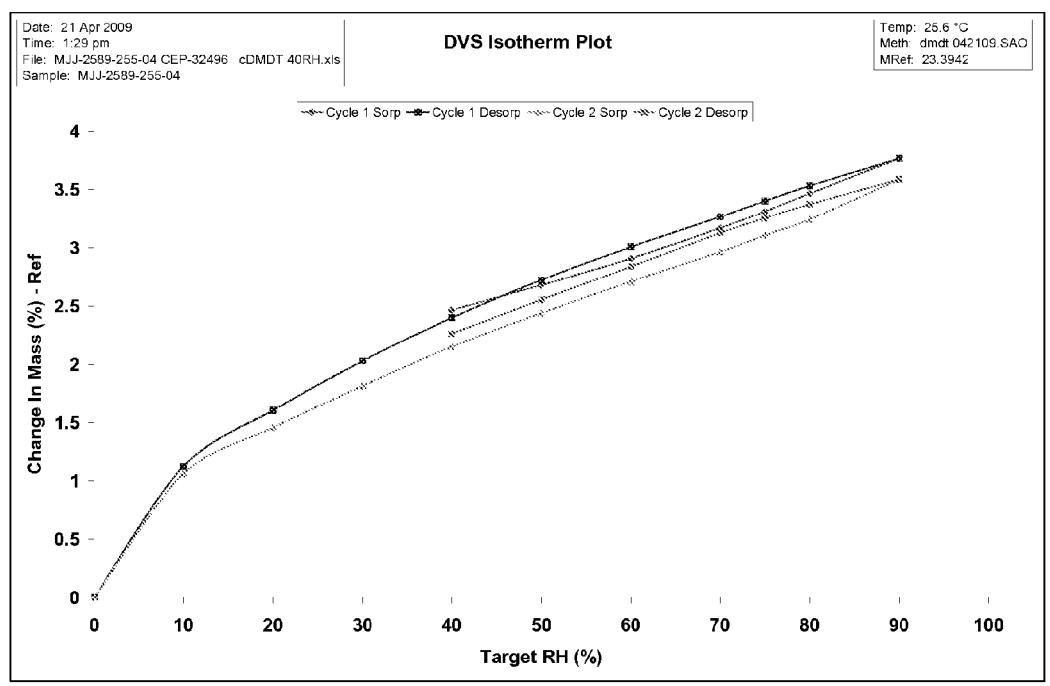

Figure 23C: Kinetic Data/Mass Plot of Malonate Form A$_1$
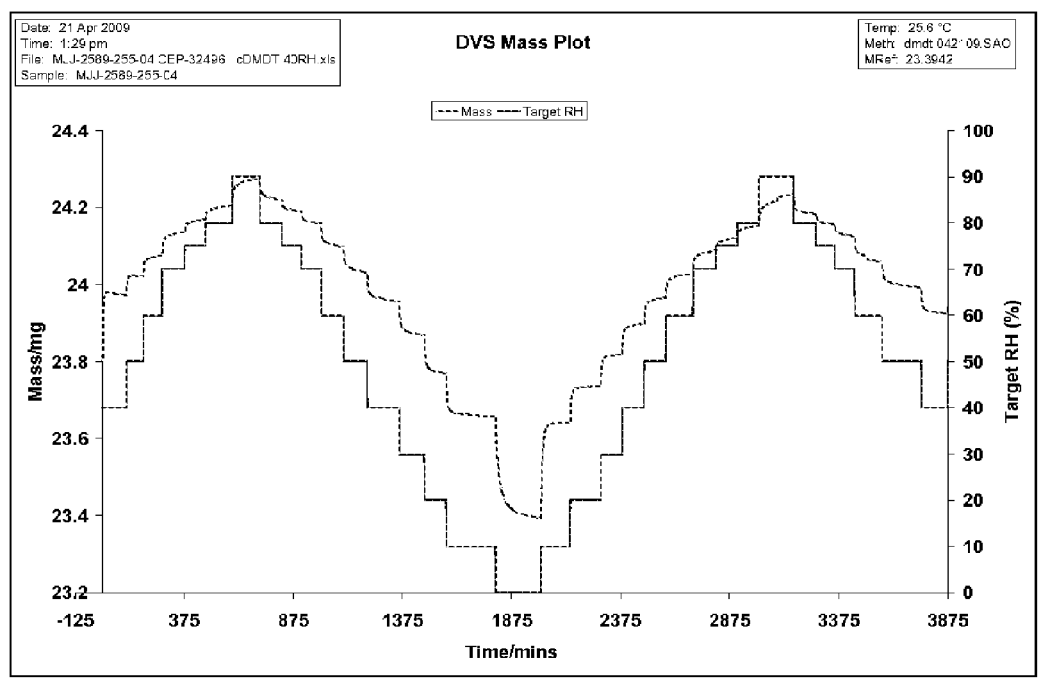

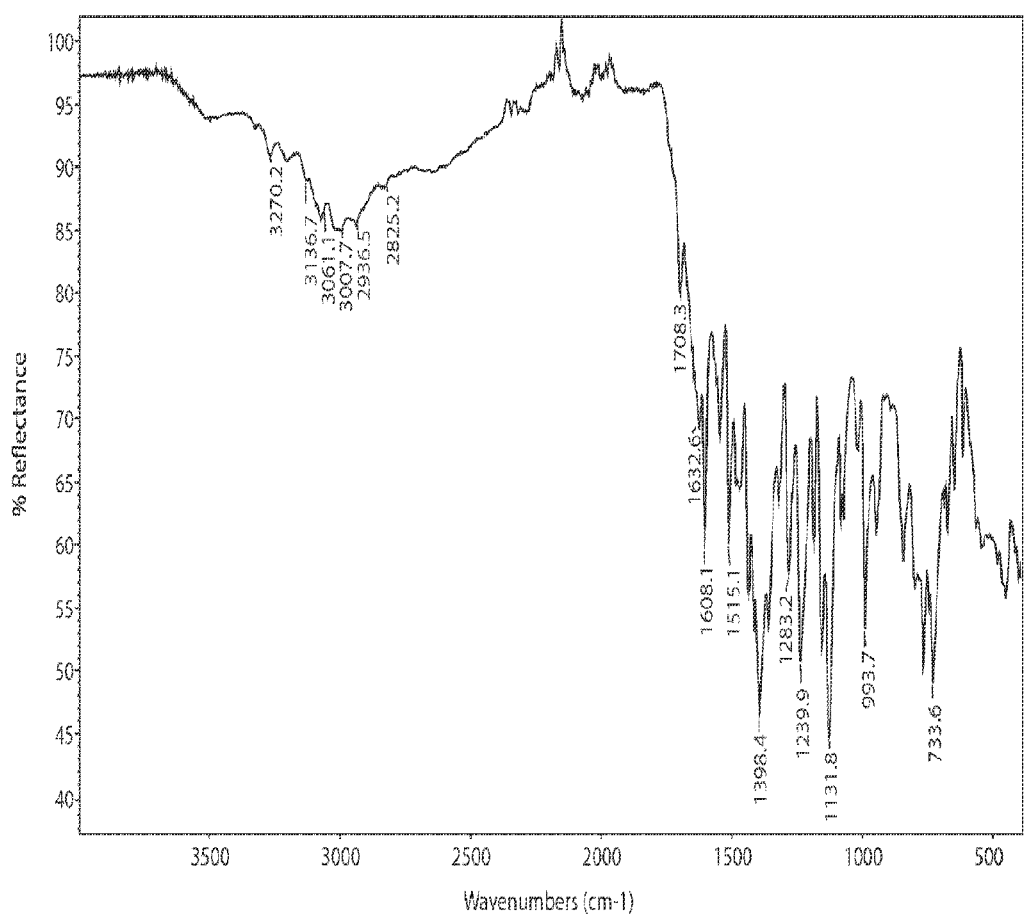
FIG. 24  FTIR Spectrum of Malonate Form A1

Figure 25: Photograph of Malonate Form A$_1$ at Room Temperature
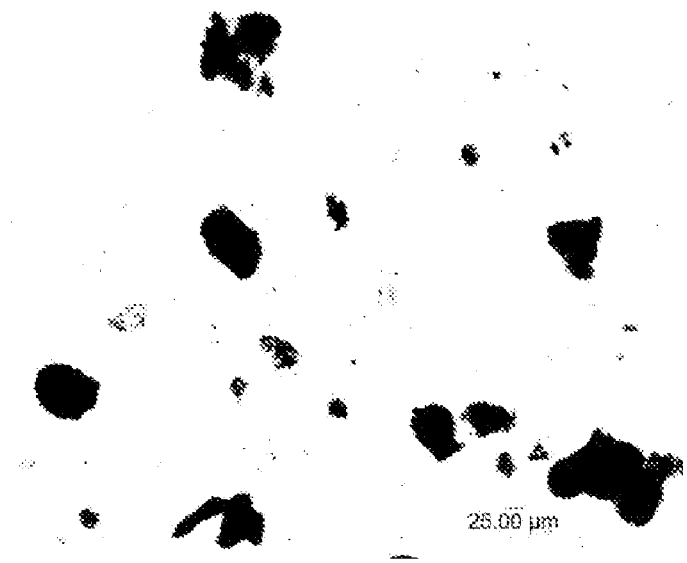

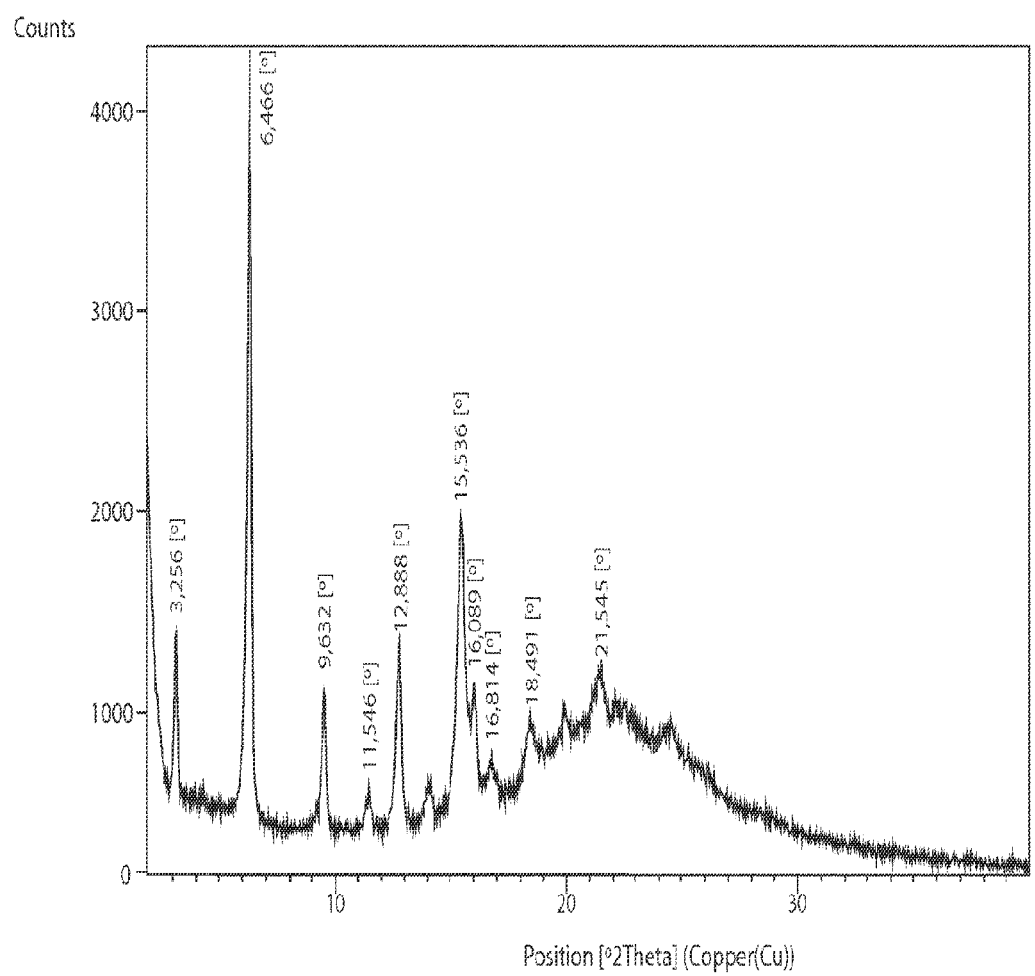
FIG. 26    XRPD Pattern of Phosphate Form $A_1$

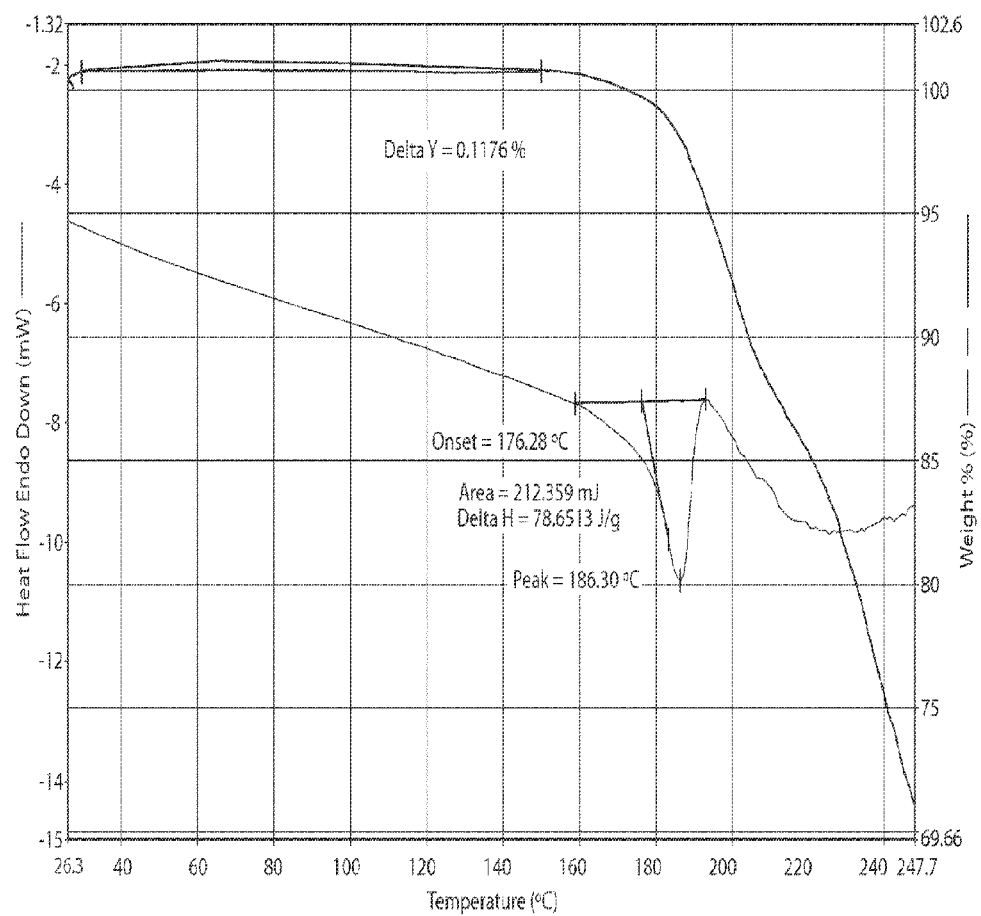
FIG. 27 Overlay of DSC and TGA Curves of Phosphate Form A1

Figure 28: GVS Isotherm of Phosphate Form A$_1$
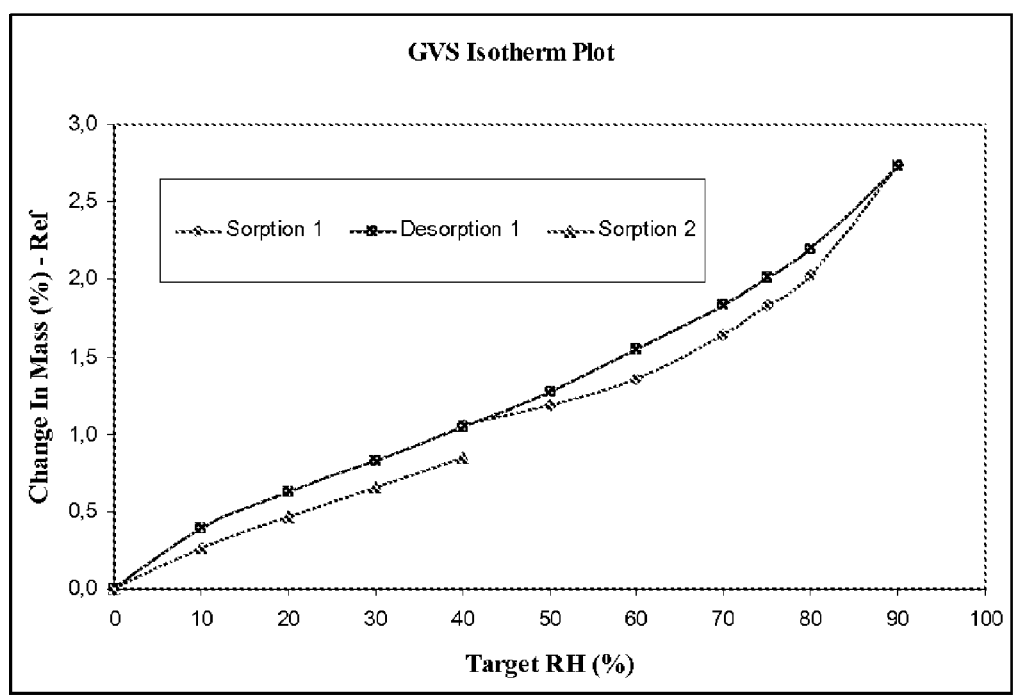

Figure 29: Kinetic Data/Mass Plot of Phosphate Form A$_1$
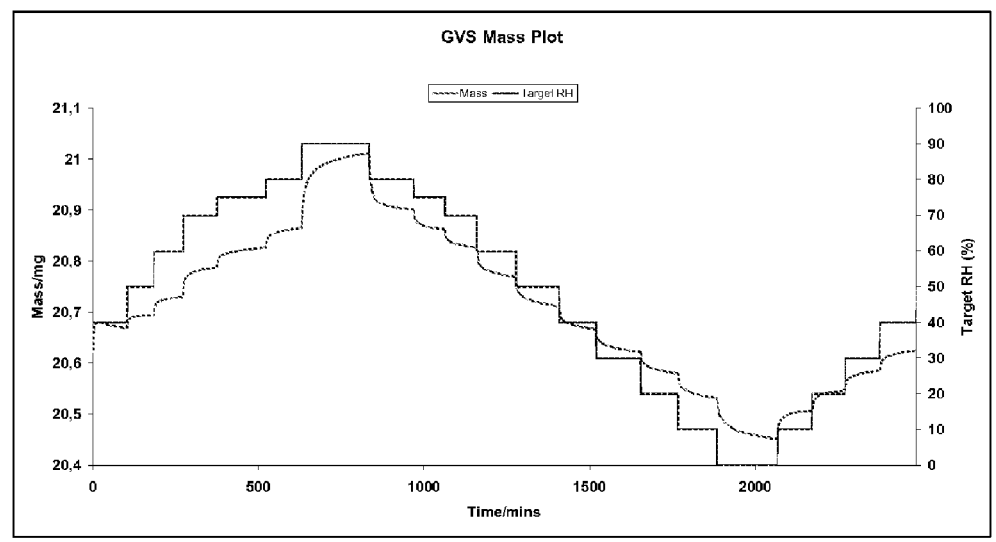

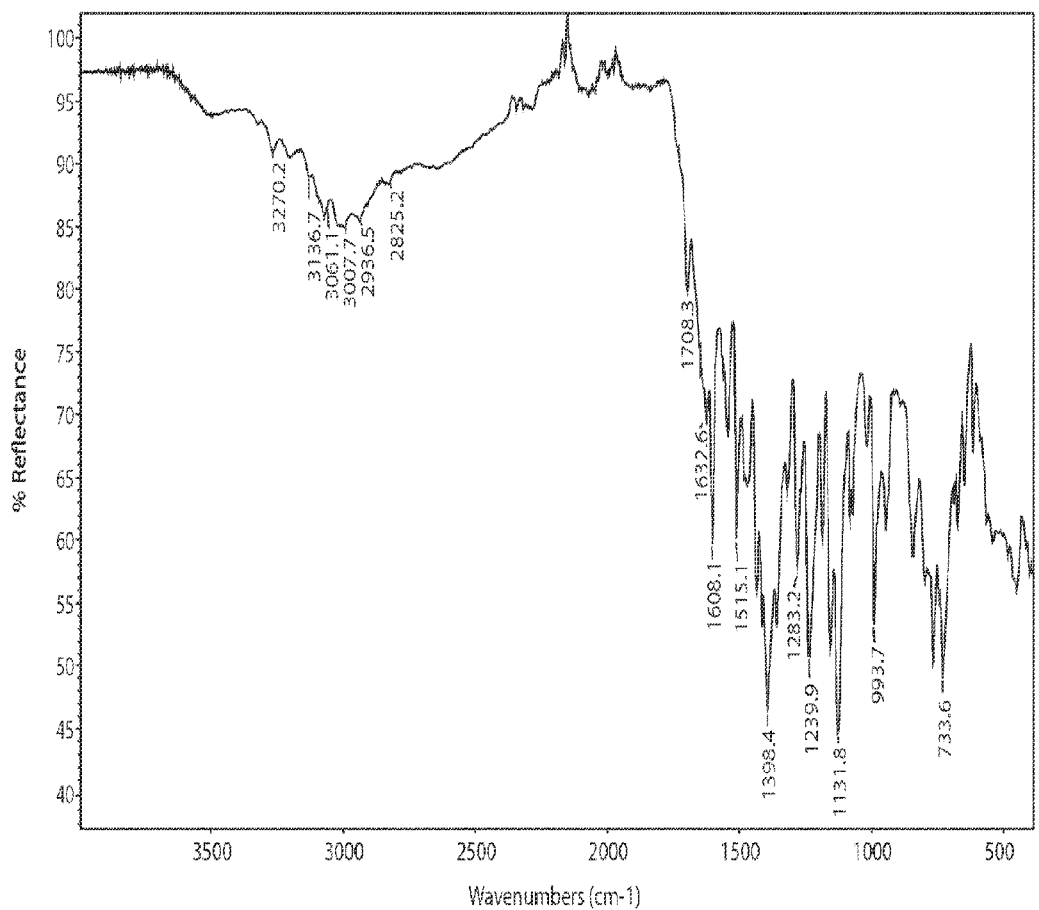
FIG. 31 FTIR Spectrum of Phosphate Form A₁

Figure 32: Photograph of Phosphate Form A$_1$ at Room Temperature
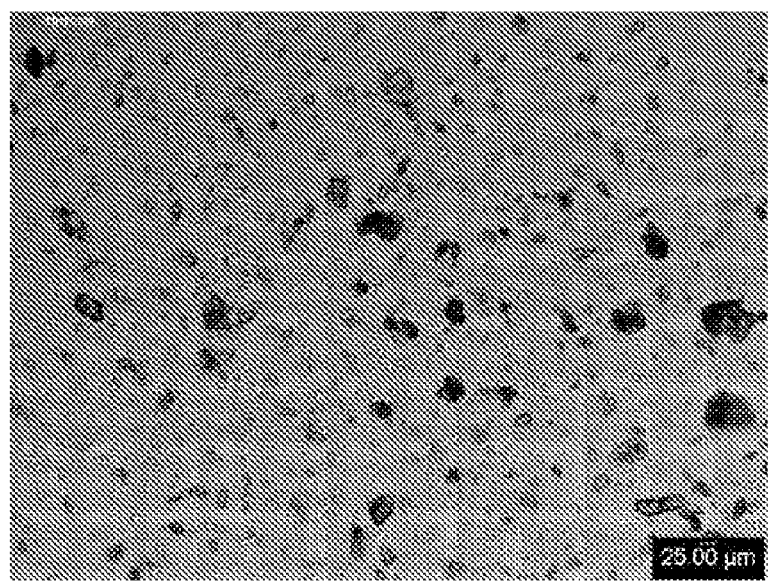

SOLID STATE FORMS OF A QUINAZOLINE DERIVATIVE AND ITS USE AS A BRAF INHIBITOR

CROSS-REFERENCE TO RELATED APPLICATIONS

This application is a continuation of U.S. application Ser. No. 14/746,666, filed Jun. 22, 2015, which is a continuation of International Application No. PCT/US2014/023110, filed Mar. 11, 2014, published in English as WO2014/164648, which claims the benefit of and priority to U.S. Provisional Patent Application No. 61/776,081, filed Mar. 11, 2013; each of the aforementioned applications is hereby expressly incorporated by reference in its entirety. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This application relates to various salts of the following compound (hereinafter referred to as Compound I)

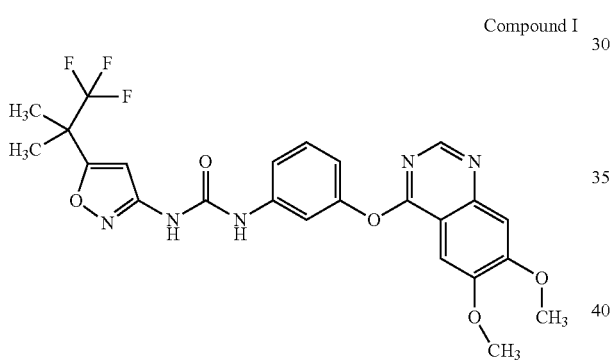

Compound I as well as solid state forms of Compound I and its salts and pharmaceutical compositions comprising the same. This application also relates to therapeutic uses of these materials and compositions.

SUMMARY OF THE INVENTION

BRAF is a member of the RAF kinase family of serine/threonine-specific protein kinases. The protein plays a role in regulating the MEK/ERK signaling pathway, which effects cell division, differentiation, and secretion. Acquired mutations in the BRAF gene (i.e., oncogene) in adults can constituently activate the kinases MEK and ERK, thereby fueling cancer growth. Several mutated forms of BRAF have been identified in cancers including melanoma, colorectal cancers, papillary thyroid carcinomas, low-grade serous ovarian cancers, and non-small cell lung cancers. The V600E mutation, which is found in the majority of cases (~80%) in these types of cancers and in over 50% of patients with melanoma, is an activating mutation resulting in approximately 500-fold greater activity relative to wild type (wt) BRAF (Curtin et al 2005, Davies et al 2002). The increase in kinase activity causes hyperstimulation of downstream signaling pathways, which can impart immortalization of and tumorigenic potential to cells. Not only is $BRAF^{V600E}$ oncogenic, but recent evidence also indicates that this genotype contributes to the development of benign lesions in various tissues, and can progress to a full malignant phenotype in the context of additional genetic events (Michaloglou et al 2008).

Inhibition of the $BRAF^{V600E}$ protein has been shown in animals and in humans to have a profound effect on tumor growth. Results from clinical studies in patients with the $BRAF^{V600E}$ mutation have shown clinically significant and statistically significant superior survival, progression-free survival, and tumor response compared with previous standard therapies. For example, vemurafenib is a $BRAF^{V600E}$ inhibitor that is approved in the United States for patients with unresectable or metastatic melanoma with the $BRAF^{V600E}$ mutation. Approximately half of patients who received vemurafenib responded favorably, with longer progression-free survival and a significant reduction in the risk of death as compared to other available therapies (Chapman et al 2011).

Various BRAF inhibitors have been reported. For example, WO 2009/117080 discloses quinazoline derivatives as modulators of RAF kinase, including BRAF kinase. Compound I has the following structure:

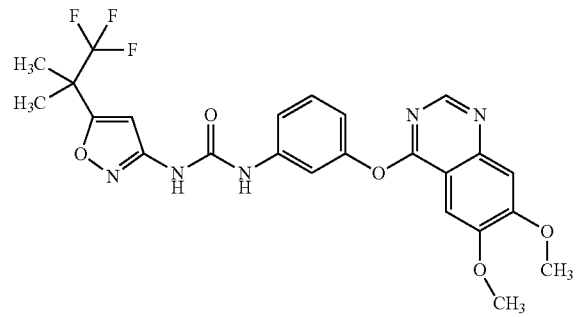

Compound I and the following chemical names: 1-[3-(6,7-dimethoxyquinazolin-4-yloxy)-phenyl]-3-[5-(2,2,2-trifluoro-1,1-dimethyl-ethyl)-isoxazol-3-yl]-urea or N-[3-[(6,7-dimethyoxy-4-quinazolinyl)oxy]phenyl]-N'-[5-(2,2,2-trifluoro-1,1-dimethylethyl)-3-isoxazolyl]urea. Compound I is a potent and selective inhibitor of BRAF kinase including mutated versions. For example, Compound I inhibits BRAF V600E at low nanomolar concentrations in vitro in intact cells as well as in isolated systems.

Different salt and/or solid state forms of Compound I can have significantly different physical properties, which either alone or in combination, can affect bioavailability. Similarly, the physical properties of the various salt/solid state forms of Compound I can also affect other aspects such as processing and storage characteristics. All of these properties are factors in selecting a salt and/or solid state form for clinical testing and commercial development.

A number of different salt forms of Compound I have been identified and are described herein. Various solid state forms of these salts as well as the solid state form of the free base of Compound I were also identified. The preparation and physical characterization of these materials are also provided herein.

The present application also provides pharmaceutical compositions comprising Compound I (free base) and/or salts of Compound I which may be used for treating various disease states such as melanoma, colorectal cancer, papillary thyroid carcinoma, low-grade serous ovarian cancer, and non-small cell lung cancer. In another aspect the present application provides pharmaceutical compositions comprising Compound I (free base) and/or salts of Compound I for treating a disease state associated with a mutated form of BRAF kinase.

BRIEF DESCRIPTION OF THE DRAWINGS

FIG. 14 is a photograph of bromide Form $A_1$ at room temperature.

FIG. 15 illustrates the XRPD pattern of chloride Form $A_1$.

FIG. 16 illustrates the variable temperature XRPD patterns of chloride Form $A_1$ (25° C.-245° C.).

FIG. 17 illustrates the overlay of DSC and TGA curves of chloride Form $A_1$.

FIG. 18 illustrates the GVS isotherm of chloride Form $A_1$.

FIG. 19 illustrates the XRPD patterns of chloride Form $A_1$ before and after GVS analysis.

FIG. 20 illustrates the FTIR spectrum of chloride Form $A_1$.

FIG. 21 is a photograph of chloride Form $A_1$ at room temperature.

FIG. 22 illustrates the XRPD pattern of malonate Form $A_1$.

FIG. 23A illustrates the overlay of DSC and TGA curves of malonate Form $A_1$.

FIG. 23B illustrates the GVS isotherm of malonate Form $A_1$

FIG. 23C illustrates a kinetic data/mass plot of malonate Form $A_1$

FIG. 24 illustrates the FTIR spectrum of malonate Form $A_1$.

FIG. 25 is a photograph of malonate Form $A_1$ at room temperature.

FIG. 26 illustrates the XRPD pattern of phosphate Form $A_1$.

FIG. 27 illustrates the overlay of DSC and TGA curves of phosphate Form $A_1$.

FIG. 28 illustrates the GVS isotherm of phosphate Form $A_1$.

FIG. 29 illustrates the kinetic data/mass plot of phosphate Form $A_1$.

FIG. 31 illustrates the FTIR Spectrum of phosphate Form $A_1$.

FIG. 32 is a photograph of phosphate Form $A_1$ at room temperature.

DETAILED DESCRIPTION OF THE PREFERRED EMBODIMENT

Figure 1:
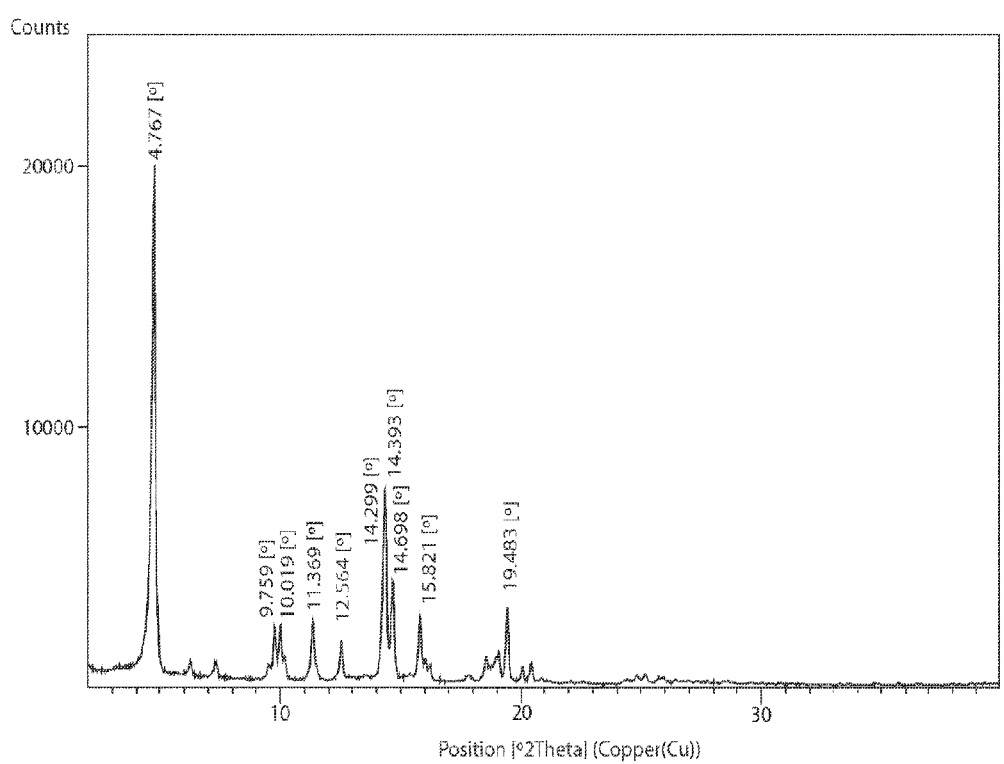
FIG. 1 illustrates the XRPD pattern of Form $A_o$.

Pharmaceutical solids (also referred to as active pharmaceutical ingredients or APIs) can exist m more than one solid state form (i.e., crystalline, noncrystalline/amorphous, quasicrystalline/organized aggregate). Polymorphism is defined as the ability of a solid compound to exist in more than one crystalline form with the same covalent chemical structure, but different supra-molecular structures and ordered arrangements of molecules within the crystalline lattice. In addition to exhibiting polymorphism, many pharmaceutical solids form hydrates and organic solvates, which themselves can be crystalline and exhibit polymorphism. Hydrates can be stoichiometric or non-stoichiometric. In a stoichiometric hydrate, the water molecules are (relatively) tightly associated with or bound to the pharmaceutical compound as well as to other water molecules and as a result are integral to the crystal lattice. In contrast, the water molecules of a non-stoichiometric hydrate (sometimes referred to as a variable hydrate) are more loosely associated with the pharmaceutical compound and the crystal lattice.

It is well recognized that different solid state forms of the same compound can exhibit significantly different chemical and physical properties including color, morphology, stability, solubility, dissolution and bioavailability. As with all pharmaceutical compounds and compositions, the chemical and physical properties of a particular solid state form of a compound are important to its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including chemical and solid state stability at ambient conditions, especially to moisture, and under storage conditions including accelerated storage conditions, i.e., high relative humidity and temperature), (4) surface properties such as surface area, wettability, interfacial tension and shape, (5) mechanical properties such as hardness, tensile strength, compactibility, handling, flow and blend; and (6) filtration properties. These properties can affect, for example, processing and storage of pharmaceutical compositions, sometimes referred to as drug product and/or of the processing and storage of an API, which is sometimes referred to as drug substance. As mentioned above, different solid state forms of the API can have different rates of solubility which can translate into differences in bioavailability in vivo.

In general, the solid state form of a compound (or salt of that compound) can be distinguished from another solid state form of the same compound (or salt) using one or more of the following techniques: x-ray powder diffraction (XRPD), thermal techniques including thermogravimetric analysis (TGA) and differential scanning calorimetry (DSC), Gravimetric Vapor Sorption (GVS), as well as Infrared (IR), Raman and/or solid state NMR (ssNMR) spectroscopy. In particular XRPD is particularly useful in identifying and/or distinguishing between polymorphs of a given compound (or salt of that compound) because it is generally accepted and understood that every crystalline phase of a given compound (or salt of that compound) produces a characteristic x-ray diffraction pattern. See generally, USP 35, <941> pp 427-431 (Dec. 1, 2012). It is also generally accepted that complementary analytical techniques can be used to confirm the identity of a particular crystalline form.

Table 1 sets forth the salts described in this application.

TABLE 1

Salts Of Compound I

| Salt Form | Solid State Description |
|---|---|
| Bromide $A_1$ | Crystalline anhydrate |
| Chloride $A_1$ | Crystalline anhydrate |
| Malonate $A_1$ | Crystalline anhydrate |
| Phosphate $A_1$ | Crystalline anhydrate |

The solid state descriptions in Table 1 were assigned primarily based upon XRPD pattern. The subscript "1" after the letter "A" was assigned to indicate the mono-salt form. As used herein, the subscript "O" is used to denote a free base (non-salt) form. One of skill in the art would readily understand that descriptors, such as, for example "the chloride salt" or "chloride-Compound I salt" or "Compound I-chloride salt", refer to the HCl (or hydrochloride) salt of Compound I.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "polymorphic" or "polymorphism" is defined as the possibility of at least two different crystalline arrangements for the same chemical molecule.

The term "solid state form" as used herein, refers to both crystalline and amorphous (non-crystalline) forms of Compound I and mixtures thereof in any ratio. It should be understood that the term solid state form includes crystalline and amorphous (non-crystalline) hydrates and solvates of Compound I as well.

The term "chemical form" as used herein, refers to a salt or non-salt (free base) forms of Compound I or mixtures thereof in any ratio. It should be understood that the term chemical form includes hydrates and solvates of Compound I as well as hydrates and solvates of salts of Compound I as well.

The term "solute" as used herein, refers to a substance dissolved m another substance, usually the component of a solution present in the lesser amount.

The term "solution," as used herein, refers to a mixture containing at least one solvent and at least one compound at least partially dissolved in the solvent.

The term "solvate," as used herein, refers to a crystalline material that contains solvent molecules within the crystal structure.

The term "solvent," as used herein, means a substance, typically a liquid, that is capable of completely or partially dissolving another substance, typically a solid. Unless otherwise specified, typical solvents for the practice of this invention include, but are not limited to, water, acetic acid, acetone, acetonitrile, 1-butanol, 2-butanol, 2-butanone, butyronitrile, tert-butanol, chlorobenzene, chloroform, cyclohexane, 1,2-dichloloroethane, dichloromethane, diethylene glycol dibutyl ether, diisopropyl amine, diisopropyl ether, 1,2-dimethoxyethane, N,N-dimethylacetamide, N,N-dimethylformamide, dimethyl sulfoxide, 1,4-dioxane, ethyleneglycoldiemethylether, ethanol, ethyl acetate, ethylene glycol, ethyl formate, formic acid, heptane, isobutyl alcohol, isopropyl acetate, isopropyl amme, methanol, methoxy benzene, methyl acetate, methyl isobutyl ketone, 2-methyltetrahydrofuran, methyl tert-butyl ether, 1:1 formamide:water, 1:1 N-methylpyrrolidinone, 2-pentanone, 3-pentanone, 1 pentanol, 1,2-propanediol, 2-propanol, 1-propanol, propanonitrile, pyridine, tetrahydrofuran, tetrahydropyran, toluene, triethyl amine, xylene, mixtures thereof and the like.

The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. A therapeutically effective amount or dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the solid state and chemical forms of the invention would be administered at lower dosage levels, with a gradual increase in dose until the desired effect is achieved.

Unless stated otherwise, percentages stated throughout this specification are weight/weight (w/w) percentages.

The term "pharmaceutically acceptable excipients," as used herein, includes any and all solvents, dispersion media, coatings, antibacterial and antifungal agents, isotonic and absorption delaying agents and the like. The use of such media and agents for pharmaceutical active substances is well known in the art, such as in *Remington: The Science and Practice of Pharmacy,* 20th ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

For therapeutic purposes, the crystalline or amorphous forms of the present invention can be administered by any means that results in the contact of the active agent with the agent's site of action in the body of the subject. The solid state forms of Compound I and/or its salts may be administered by any conventional means available for use in conjunction with pharmaceuticals, either as individual therapeutic agents or in combination with other therapeutic agents, such as, for example, analgesics. The solid and chemical forms of the present invention are preferably administered in therapeutically effective amounts for the treatment of the diseases and disorders described herein to a subject that has been determined to be in need of such treatment.

Typical dose ranges are from about 0.01 mg/kg to about 500 mg/kg of body weight per day. A preferred unit dose for an adult human includes about 25, 50, 100 and 200 mg of the selected solid state form or chemical form of Compound I, which may be administered one to four times a day. In an alternate method of describing a therapeutically effective dose, is a particular dose that is necessary to achieve a particular blood serum level.

The solid state and/or chemical forms of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20th ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions of the present invention can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the aforementioned excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Non-aqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicyclate.

Solvents and Acids

The $pK_a$ values of Compound I were calculated by ACD Software, version 101. The $pK_a$ of 2.8 for the quinazoline moiety suggests that for salt screening may be attempted with a wide range of acids. This does not, however, guarantee or predict success for all conditions or for all acids that were selected for testing. Salt or co-crystal formation was attempted with the 24 acids listed in Table 2. These acids were selected on the basis of $pK_a$ and acceptability by regulatory authorities (Class 1, 2 and 3). See generally, Stahl, Heinrich P., Wermuth, Camile G., Editors, 2002. *Handbook of Pharmaceutical Salts: Properties, Selection, and Use*, Verlag Helvetica Chimica Acta, and Wiley-VCR. Weinheim. Germany and Switzerland; Bundavari, Susan, Editor, 1996, *Merck Index, Twelfth Edition*, Merck and Company, Inc., Whitehouse Station, N.J., USA.

As a general rule, salt formation is more likely to result when the difference between the $pK_a$ of the acid and the $pK_a$ of the anhydrous free base of Compound I (Form Ao) is greater than 2, whereas co-crystals are more likely when the pKa difference is less than 2. The application of co-crystal technologies has only recently become more recognized as a way to enhance the solubility and stability of certain APIs. The 24 acids listed in Table 2 were generally thought to be more likely to yield salt formation over cocrystal formation. Each Form $A_0$/acid combination was subject to maturation, slow cooling and evaporation crystallization techniques in 3 different solvents. In the experiments described herein reagent-grade acetone, chloroform, and tetrahydrofuran were used without further purification.

TABLE 2

Name, Pk$_a$ Value And Melting Points Of Various Acids

| Acid | Acidity (pKa) | Melting point (° C.) |
|---|---|---|
| Acetic acid | 4.76 | Liquid |
| Ascorbic acid | 4.17, 11.6 | 190-192 |
| Benzoic acid | 4.21 | 122.4 |
| Citric acid | 3.15, 4.77, 6.40 | 153 |
| Ethanesulfonic acid | 2.05 | Liquid |
| Fumaric acid | 3.03, 4.44 | 287 |
| Glutamic acid, DL | 2.19, 4.25, 9.67 | 300 |
| Glutaric acid | 4.34, 5.42 | 95-98 |
| Hippuric acid | 3.55 | 187-188 |
| Hydrobromic acid (48% aq) | −6 | Liquid |
| Lactic acid | 3.85 | 16.8 |
| L - Tartaric acid | 2.98, 4.34 | 171-174 |
| L - Pyroglutamic acid | 3.32 | 160-163 |
| Maleic acid | 1.92, 6.27 | 131-139 |
| Malonic acid | 2.83 | 135-136 |
| Nicotinic acid | 4.75 | 236 |
| Octanoic acid | 4.89 | Liquid |
| Orotic acid | 5.85, 8.95 | 345 |
| Ortho Phosphoric acid | 2.12, 7.21, 12.67 | Liquid |
| Propionic acid | 4.88 | Liquid |
| Sodium bisulfate monohydrate | 1.9 | 74 |
| Succinic acid | 4.21, 5.64 | 185 |
| Sulfuric acid | −3 | Liquid |
| Toluenesulfonic acid, p- | −2.8 | 106 |

X-Ray Powder Diffraction (XRPD)

Powder X-ray diffraction patterns were recorded on a PANalytical X Pert Pro diffractometer equipped with an X celerator detector using Cu Kα radiation at 45 kV and 40 mA. Kα1 radiation is obtained with a highly oriented crystal (Ge111) incident beam monochromator. A 10 mm beam mask, and fixed (¼°) divergence and anti-scatter (½°) slits were inserted on the incident beam side. A fixed 5 mm receiving slit and 0.04 Soller block were inserted on the diffracted beam side. The sample was rotated on a PANalytical PW3065/12 Spinner (15 revolutions I min). The typical X-ray powder pattern scan was collected from ca. 2 to 40° 2θ with a 0.0080° step size and 96.06 sec counting time which resulted in a scan rate of approximately 0.5°/min. The samples were spread on silicon zero background (ZBG) plate for the measurement. For screening studies, the samples were spread on either ZBG or glass plates and were measured from ca. 2 to 35° 2θ with a 0.0334° step size and 31.75 sec counting time which resulted in a scan rate of approximately 7.1°/min. Measurement of the Si reference standard before the data collection resulted in values for 2θ and intensity that were well within the tolerances of 28.42<2θ<28.48 and significantly greater than the minimum peak height of 150 cps.

Variable Temperature X-Ray Powder Diffraction (VT-XRPD)

Variable temperature studies were performed with an Anton Paar TTK450 temperature chamber under computer control through an Anton Paar TCU100 temperature control unit. Typically the measurements were done with a nitrogen flow through the camera. Two measurement schemes were used, restricted and continuous. In the restricted mode, measurements were made after the TK450 chamber reached the requested temperature. In the continuous mode, the sample was heated at 10° C./minute and fast scans were measured as the temperature changed. After the requested temperature was reached, the sample was cooled at 35° C./minute and a slow scan measured 25° C. The temperatures chosen were based on DSC results. For the diffractometer set-up a 10 mm beam mask, 0.04 radian Soller block, fixed (¼°) divergence and anti-scatter (½°) slits were inserted on the incident beam side. A fixed 5 mm receiving slit, 0.04 radian Soller slits and a 0.02 mm Nickel filter were inserted on the diffracted beam side. The slow scans were collected from ca. 3 to 40° 2θ with a 0.0080° step size and 100.97 sec counting time which resulted in a scan rate of approximately 0.5°/min. The fast scans were collected from ca. 3 to 30° 2θ with a 0.0167° step size and 1.905 sec counting time which resulted in a scan rate of approximately 44°/min.

Differential Scanning Calorimetry (DSC)

Thermal curves were acquired using a Perkin-Elmer Sapphire DSC unit equipped with an autosampler running Pyris software version 6.0 calibrated with Indium prior to analysis. Solid samples of 1-10 mg were weighed into 20 μL aluminum samples pin with a pin-hole pan. The DSC cell was then purged with nitrogen and the temperature heated from 0 to 300° C. at 10° C. I min. Indium (Tm=156.6° C.; ΔHFUS=28.45 J g−1) was used for calibration.

Thermogravimetric Mass Spectrometry (TGA-MS)

Thermal curves were acquired using a Perkin-Elmer Pyris 1 TGA unit running Pyris software version 6.0 calibrated with alumel (95% nickel, 2% manganese, 2% aluminum and 1% silicon), nickel and calcium oxalate monohydrate. TGA samples between 1-5 mg were monitored for percent weight loss as heated from 25 to 250° C. at 10° C./min in a furnace purged with Helium at ca. 50 mL/min. To simultaneously follow the evolution of the gaseous decomposition products over the temperature range investigated, the thermobalance was connected to a Thermo Star Quadrupole Mass Spectrometer (Asslar, Germany). The transfer line to introduce gaseous decomposition products into the mass spectrometer was a deactivated fused silica capillary (SGE Analytical science, Fused Silica (100% Methyl Deactivated), 220 mm OD, 150 mm ID, Australia) temperature controlled to 200° C. to avoid possible condensation of the evolved gases. In this way the TGA weight loss and the mass spectrometric ion intensity curves of the selected ionic species could be recorded simultaneously.

Gravimetric Vapor Sorption (GVS)

GVS experiments have been carried out using the DVS-HT instrument (Surface Measurement Systems, London, UK). This instrument measures the uptake and loss of vapor gravimetrically using a recording ultra-microbalance with a mass resolution of ±0.1 μg. The vapor partial pressure (±1.0%) around the sample is controlled by mixing saturated and dry carrier gas streams using electronic mass flow controllers. The desired temperature is maintained at ±0.1° C. The samples (1-10 mg) were placed into the DVSHT and DVS-1 instruments at the desired temperature.

The sample was loaded and unloaded at 40% RH and 25° C. (typical room conditions). A moisture sorption isotherm was performed as outlined below (2 scans giving 1 complete cycle). The software uses a least squares minimization procedure together with a model of the mass relaxation, to predict an asymptotic value. The measured mass equilibration value must be within 2% of that predicted by the software before the next % RH value is selected. The minimum equilibration time was set to 1 hour and the maximum to 4 hours.

Fourier Transform Infrared (FTIR) Spectroscopy

Spectra were obtained using a Thermo Electron-Nicolet Avatar 370 DTGS instrument with the Smart Orbit ATR attachment containing a diamond crystal window. Thermo Electron Omnic™ software (version 3.1) was used to compute the spectrum from 4000 to 400 cm-1 from the initial interferogram. A background scan was collected before spectral resolution and averaged. Assignments of the absorption frequencies were made using Know It All software (version 8.0).

Optical Microscopy (OM)

Microscopic observation of the sample morphology was performed using an Olympus B60 polarized light microscope. Samples were suspended in mineral oil and compressed on a glass slide with a cover slip prior to observation. Images were taken with a FW-24 (PAX CAM) camera. A 10× objective coupled with an additional 10× magnification from the microscope optics gave a total magnification of 100×. The Pax-it software (version 6.2) was used to analyze and photograph the images.

Identity, Assay, and Purity by HPLC

Typically 1-5 mg of samples were diluted to 10 mL with sample solvent (1:1 (v:v) Mobile phase A:Mobile phase B) and the assay concentrations were determined from an average of duplicate injections using the following HPLC method. The purity and impurity analyses are done using conventional HPLC.

| | |
|---|---|
| Column: | Zorbax SB-CN, 1.8 µm, 50 × 4.6 mm (length × ID) |
| Col. Pre-Filter: | OptiSolv EXP 0.2 µm |
| Column Temp: | 50° C. |
| Detector: | UV, 280 nm |
| Inject: | 10 µL |
| Flow rate: | 0.8 mL/min. |
| Mobile phases: | A. 15 mM Ammonium Acetate (aq.), pH = 4.0 |
| | B 100% Methanol |

| Gradient: | | |
|---|---|---|
| Time (min.) | % A | % B |
| 0.0 | 80 | 20 |
| 4.0 | 50 | 50 |
| 9.5 | 50 | 50 |
| 14.0 | 20 | 80 |
| 18.0 | 20 | 80 |
| 18.5 | 80 | 20 |
| 22.0 | 80 | 20 |

Determination of Solid-State Stability

Samples of Compound I free base and its salts (approximately 10 mg each) were stored at 40° C./75% RH in open glass vials (4 cm³) over four weeks without desiccant.

Solubility of Form Ao

The following procedure was used to assess the solubility of the anhydrous free base of Compound I (Form $A_0$) in a range of nine organic solvents listed in Table 3. Using 1.8 mL HPLC vials, approximately 10 mg of Form $A_0$ was stirred at the boiling point in 200 µL of nine different solvents. If the solid did not dissolve, an additional 100, 200 or 500 µL of solvent was added with heating to the boiling point. The additions were stopped when the solid dissolved or when 1000 µL had been dispensed. The best solubility for Form Ao was observed in acetone, chloroform, and tetrahydrofuran. Methyl t-butyl ether was chosen as an antisolvent (<10 mg/mL).

TABLE 3

Solubility Of Form $A_0$ In Different Solvents

| Solvent | Boiling Point (° C.) | Solubility Estimate at The Boiling Point |
|---|---|---|
| Acetone | 56.5 | >50 mg/mL |
| Acetonitrile | 82.0 | <20 mg/mL |
| Chloroform | 61.2 | >50 mg/mL |

TABLE 3-continued

Solubility Of Form $A_0$ In Different Solvents

| Solvent | Boiling Point (° C.) | Solubility Estimate at The Boiling Point |
|---|---|---|
| Ethyl Acetate | 77.1 | <30 mg/mL |
| Methanol | 64.7 | <20 mg/mL |
| Methyl-t-butyl Ether | 55.2 | <10 mg/mL |
| Dichloromethane | 40.0 | >20 mg/mL |
| Tetrahydrofuran | 66.0 | >50 mg/mL |
| Toluene | 110.6 | <30 mg/mL |

Characterization of Salts of Compound I

Crystallizations studies were performed on Form Ao to investigate salt formation. Maturation, slow cooling and evaporation techniques were employed to obtain different salts of Compound I. When possible, full characterization was performed on the new forms that were generated. This characterization consisted of: X-ray powder diffraction and variable-temperature X-ray powder analysis; thermal analysis; gravimetric vapor sorption; Fourier transform infrared spectroscopy, and optical microscopy.

Maturation Experiments with Acetone

For each of the acids listed below, the quantity calculated to give approximately 1.05 equivalents of acid per 20 mg of free base was weighed into a glass vial. If the acid was liquid, the density was used to determine a volume necessary to give equal mass. One mL of Form Ao dissolved in acetone (20 mg/1 mL) was added to the vial. The resulting mixtures were slurried for a total of 96 hours with alternating 4 hour periods at 50° C. and 5° C. (±0.5° C./min) using a HEL Polyblock™ Unit. The solid material was isolated by filtration, dried at 40° C. for 18 hours under house vacuum and analyzed by XRPD, DSC, and TGA. A summary of the results are shown in Table 4. The crystallization experiments were carried out in glass vials (1.5 mL, 32×11.6 mm).

TABLE 4

Maturation Study Results For Acetone

| Salt | X-ray Result | DSC | TGA* |
|---|---|---|---|
| Hydrobromic acid (48% aq) | New pattern | 229.2° C., 238.9° C. | 0.04% |
| Malonic acid | New pattern | 171.7° C. | 1.7% |
| Ortho-Phosphoric acid (85%) | New pattern | 186.3° C. | 0.1% |

*Weight loss from 25 to 150° C.

Maturation Experiments with Chloroform

For each of the acids listed below, the quantity calculated to give approximately 1.05 equivalents of acid per 20 mg of free base, was weighed into a glass vial. If the acid was liquid, the density was used to determine a volume necessary to give equal mass. One mL of Form Ao dissolved in chloroform (20 mg I 1 mL) was added to the vial. The resulting mixtures were slurried for a total of 96 hours with alternating 4 hour periods at 50° C. and 5° C. (±0.5° C./min) using a HEL Polyblock™ Unit. The solid material was isolated by filtration, dried at 40° C. for 18 hours under house vacuum and analyzed by XRPD, DSC, and TGA. The results are shown in Table 5. The crystallization experiments were carried out in glass vials (1.5 mL, 32×11.6 mm).

TABLE 5

Maturation Study Results For Chloroform

| Salt | X-ray Result | DSC | TGA* |
|---|---|---|---|
| Hydrobromic acid (48% aq) | New pattern | 68.7° C., 187.4° C., 210.3° C. | 3.7% |
| Malonic acid | New pattern | 52.52° C., 131.8° C., 163.0° C. | 14.0% |
| Ortho-Phosphoric acid (85%) | Amorphous | 142.1° C. | 10.8% |

*Weight loss from 25 to 150° C.

Maturation Experiments with Tetrahydrofuran

For each of the acids listed below, the quantity calculated to give approximately 1.05 equivalents of acid per 20 mg of free base, was weighed into a glass vial. If the acid was liquid, the density was used to determine a volume necessary to give equal mass. One mL of Form Ao dissolved in tetrahydrofuran (20 mg/1 mL) was added to the vial. The resulting mixtures were slurried for a total of 96 hours with alternating 4 hour periods at 50° C. and 5° C. (±0.5° C./min) using a HEL Polyblock™ Unit. The solid material was isolated by filtration, dried at 40° C. for 18 hours under house vacuum and analyzed by XRPD, DSC, and TGA. The results are shown m Table 6. The crystallization experiments were carried out m glass (1.5 mL, 32×11.6 mm).

TABLE 6

Maturation Study Results For Tetrahydrofuran

| Salt | X-ray Result | DSC | TGA* |
|---|---|---|---|
| Hydrobromic acid (48% aq) | New pattern | 189.2° C. weak, 227.8° C. | 0.2% |
| Malonic acid | New pattern | 169.7° C. | 3.4% |
| Ortho-Phosphoric acid (85%) | New pattern | 180.5° C. | 0.4% |

*Weight loss from 25 to 150° C.

Slow Cool Experiments with Acetone

For each of the acids listed in the table below, the quantity calculated to give approximately 1.05 equivalents of acid per 20 mg of free base, was weighed into a glass vial. If the acid was liquid, the density was used to determine a volume necessary to give equal mass. One mL of Form Ao dissolved in acetone (20 mg I 1 mL) was added to the vial. The samples were heated from 20° C. to 80° C. at a rate of 5° C./min and after 60 minutes cooled at a slow rate (−0.25° C./min) to a final temperature of 5° C. and kept at that temperature for 18 h using the HEL Polyblock™ Unit. The solid material was isolated by filtration, dried at 40° C. for 18 hours under house vacuum and analyzed by XRPD, DSC, and TGA. The results are shown in Table 7. The crystallization experiments were carried out in glass vials (1.5 mL, 32×11.6 mm).

TABLE 7

Maturation Study Results For Acetone

| Salt | X-ray Result | DSC | TGA* |
|---|---|---|---|
| Hydrobromic acid (48% aq) | New pattern | 228.3° C. | 0.2% |
| Malonic acid | New pattern | 61.5° C., 167.7° C. | 2.7% |
| Ortho-Phosphoric acid (85%) | New pattern | 58.0° C., 185.3° C. | 0.9% |

*Weight loss from 25 to 150° C.

Slow Cool Experiments with Chloroform

For each of the acids listed in the table below, the quantity calculated to give approximately 1.05 equivalents of acid per 20 mg of free base was weighed into a glass vial. If the acid was liquid, the density was used to determine a volume necessary to give equal mass. One mL of Form Ao dissolved in chloroform (20 mg I 1 mL) was added to the vial. The samples were heated from 20° C. to 80° C. at a rate of 5° C./min and after 60 minutes cooled at a slow rate (−0.25° C./min) to a final temperature of 5° C. and kept at that temperature for 18 h using the HEL Polyblock™ Unit. The solid material was isolated by filtration, dried at 40° C. for 18 hours under house vacuum and analyzed by XRPD, DSC, and TGA. The results are shown in Table 8. The crystallization experiments were carried out in glass vials (1.5 mL, 32×11.6 mm).

TABLE 8

Maturation Study Results For Chloroform

| Salt | X-ray Result | DSC | TGA* |
|---|---|---|---|
| Hydrobromic acid (48% aq) | New pattern | 181.9° C., 221.9° C. | 1.1% |
| Malonic acid | New pattern | 49.2° C., 127.3° C., 160.8° C. | 12.5% |
| Ortho-Phosphoric acid (85%) | Amorphous | 180.5° C. | 7.9% |

*Weight loss from 25 to 150° C.

Slow Cool Experiments with Tetrahydrofuran

For each of the acids listed in the table below, the quantity calculated to give approximately 1.05 equivalents of acid per 20 mg of free base, was weighed into a glass vial. If the acid was liquid, the density was used to determine a volume necessary to give equal mass. One mL of Form Ao dissolved in tetrahydrofuran (20 mg/1 mL) was added to the vial. The samples were heated from 20° C. to 80° C. at a rate of 5° C./min and after 60 minutes cooled at a slow rate (−0.25° C./min) to a final temperature of 5° C. and kept at that temperature for 18 h using the HEL Polyblock™ Unit. The solid material was isolated by filtration, dried at 40° C. for 18 hours under house vacuum and analyzed by XRPD, DSC, and TGA. The results are shown in Table 9. The crystallization experiments were carried out in glass vials (1.5 mL, 32×11.6 mm).

TABLE 9

Slow Cool Study Results for Tetrahydrofuran

| Salt | X-ray Result | DSC | TGA* |
|---|---|---|---|
| Hydrobromic acid (48% aq) | New pattern | 227.9° C. | 0.6% |
| Malonic acid | New pattern | 167.1° C., 198.4° C. | 3.1% |
| Ortho-Phosphoric acid (85%) | New pattern | 188.8° C. | 0.7% |

*Weight loss from 25 to 150° C.

Evaporation Experiments in Acetone

For each of the acids listed in the table below, the quantity calculated to give approximately 1.05 equivalents of acid per 20 mg of free base was weighed into a glass vial. If the acid was liquid, the density was used to determine a volume necessary to give equal mass. One mL of Form $A_0$ dissolved in acetone (20 mg/1 mL) was added to the vial. Approximately 20 mg of Form $A_0$ was added to the vial (20 mL, 26×58 mm). The solutions or mixtures were allowed to slowly evaporate to dryness under ambient conditions. Resulting solids were analyzed by XRPD, DSC, and TGA. The results are shown in Table 10.

TABLE 10

Evaporation Study Results for Acetone

| Salt | X-ray Result | DSC | TGA* |
|---|---|---|---|
| Hydrobromic acid (48% aq) | New pattern | 226.4° C. | 0.1% |
| Malonic acid | New pattern | 70.1° C., 114.7° C., 171.9° C. | (—) |
| Ortho-Phosphoric acid (85%) | No peaks | 75.9° C., 141.1° C. | 3.7% |

*Weight loss from 25 to 150° C.

Evaporation Experiments in Chloroform

For each of the acids listed in the table below, the quantity calculated to give approximately 1.05 equivalents of acid per 20 mg of free base was weighed into a glass vial. If the acid was liquid, the density was used to determine a volume necessary to give equal mass. Approximately 20 mg of Form $A_0$ was added to the vial (20 mL, 26×58 mm). Chloroform was added in 0.5 to 1.0 mL increments followed by heating with stirring to the boiling point. If a clear solution was achieved, the incremental additions were stopped. If a clear solution was not observed when a total of 10 mL of solvent was added, the mixture was syringe filtered (5μ Nylon membrane) into a clean vial. The solutions were allowed to slowly evaporate to dryness under ambient conditions. Resulting solids were analyzed by XRPD, DSC, and TGA. The results are shown in Table 11.

TABLE 11

Evaporation Study Results

| Salt | X-ray Result | DSC | TGA* |
|---|---|---|---|
| Hydrobromic acid | Amorphous | 180.0° C. 2.4% | 2.4% |
| Malonic acid | New pattern | 128.7° C., 137.9° C., 161.8° C. | 27.9% |
| Ortho-Phosphoric acid | New pattern | 178.8° C. | 9.2% |

*Weight loss from 25 to 150° C.

Evaporation Experiments in Tetrahydrofuran

For each of the acids listed in the table below, the quantity calculated to give approximately 1.05 equivalents of acid per 20 mg of free base was weighed into a glass vial. If the acid was liquid, the density was used to determine a volume necessary to give equal mass. Approximately 20 mg of Form Ao was added to the vial (20 mL, 26×58 mm). Tetrahydrofuran was added in 0.5 to 1.0 mL increments followed by heating with stirring to the boiling point. If a clear solution was achieved, the incremental additions were stopped. If a clear solution was not observed when a total of 10 mL of solvent was added, the mixture was syringe filtered (5μ Nylon membrane) into a clean vial. The solutions were allowed to slowly evaporate to dryness under ambient conditions. Resulting solids were analyzed by XRPD, DSC, and TGA. The results are shown in Table 12.

TABLE 12

Evaporation Study Results for Tetrahydrofuran

| Salt | X-ray Result | DSC | TGA* |
|---|---|---|---|
| Hydrobromic acid | New pattern | 225.1° C. | 1.7% |
| Malonic acid | New pattern | 65.6° C., 168.3° C. | 4.3% |
| Ortho-Phosphoric acid | Amorphous | 62.8° C. | 6.2% |

*Weight loss from 25 to 150° C.

Summary of Salt Results

One stable crystalline form of Form $A_0$ was identified (See Table 13). In several cases, Form Ao precipitated from solution with no indication of salt formation. Data pertaining to four salts is shown in Tables 12 and 14. A detailed characterization of these salts is also described in this application.

TABLE 13

Characterization Data Form $A_0$

| Form | XRPD | DSC(° C.) | TGA[1] | GVS[2] | XRPD[3] | Purity (%) |
|---|---|---|---|---|---|---|
| $A_0$ | Crystalline | 236.0 | 0.2 | 1.3 | No change | 98.3 |

N/A = Not Available
[1]Weight loss 25° C. to 120° C.
[2]Percent increase in mass at 90% RH
[3]After GVS analysis

TABLE 14

Characterization Data For Isolated Salts

| Salt | XRPD | DSC (° C.) | TGA[1] | GVS[2] | XRPD[3] | Purity (%) |
|---|---|---|---|---|---|---|
| Bromide $A_1$ | Crystalline | 230.9 | 0.1 | 1.0 | No change | 98.4 |
| Chloride $A_1$ | Crystalline | 236.1 | 0.2 | 1.7 | No change | N/A |
| Malonate $A_1$ | Crystalline | 171.7 | 1.7 | N/A | N/A | 98.6 |
| Phosphate $A_1$ | Crystalline | 186.3 | 0.1 | 2.7 | No change | 95.8 |

N/A = Not Available
[1]Weight loss 25° C. to 120° C.
[2]Percent increase in mass at 90% RH
[3]After GVS analysis Solid State Analysis Compound I Free Base, Form $A_0$ Preparation from Form $A_0$ To a 10 L Chemglass jacketed reactor with $N_2$ inlet/outlet was added compound 2 (200.0 g, 637 mmol), compound 3 (177.0 g, 596 mmol) and 4-Dimethylaminopyridine (DMAP) (2.88 g) followed by 4.0 L of isopropyl acetate. The internal temperature was raised to 70° C. and heated for 9 hours. The reaction remained a slurry throughout the reaction and HPLC showed no compound 2 remaining after heating for that period. Next, 2.0 L of heptane were added at 70° C. and the reaction cooled to 20° C. The solids were stirred for 1 hour, filtered and the cake washed with 2.0 L of 1:1 isopropyl acetate/heptanes. The white solids were placed in an oven with N2 bleed at 55° C. under 75 mbar vacuum. The resulting solids weighed 295 g (96% yield) of Form $A_0$ with 99.3% purity by HPLC.

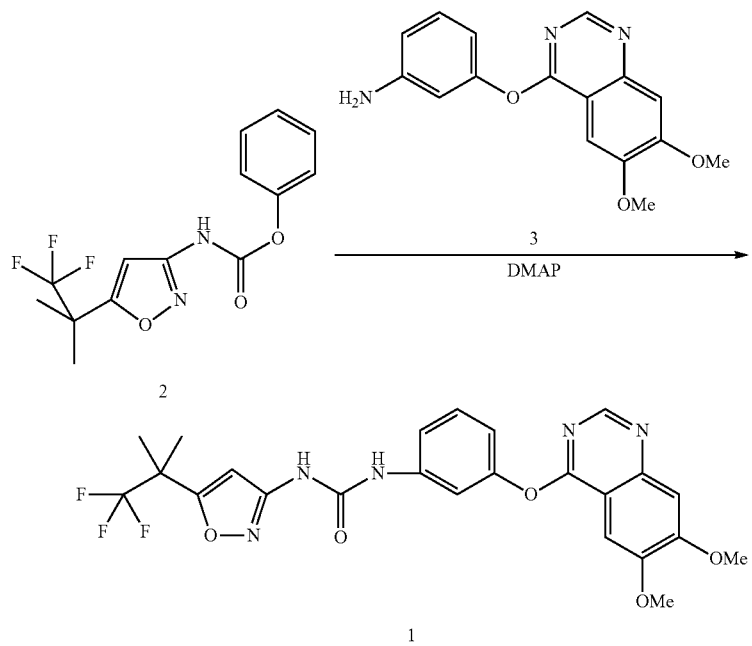

Characterization by XRPD

The X-ray diffraction pattern characteristic of the crystalline Form $A_0$ is shown in 5 Table 15 and FIG. 1.

TABLE 15

Select Two Theta Positions (2θ), D-Spacings (d) And Relative Intensities (I) Of XRPD

| No. | Pos. [2θ.] | d-spacing [Å] | Rel. Int. [%] |
|---|---|---|---|
| 1 | 4.77 | 18.52 | 100 |
| 2 | 9.76 | 9.06 | 10 |
| 3 | 9.80 | 9.02 | 9 |
| 4 | 10.02 | 8.82 | 11 |
| 5 | 11.37 | 7.78 | 11 |
| 6 | 12.56 | 7.04 | 8 |
| 7 | 14.30 | 6.19 | 27 |
| 8 | 14.39 | 6.15 | 36 |
| 9 | 14.70 | 6.02 | 19 |
| 10 | 15.82 | 5.60 | 13 |
| 11 | 19.10 | 4.64 | 5 |
| 12 | 19.48 | 4.55 | 13 |

The highest peak (intensity 100%) is set in bold letters.

Characterization by VT-XRPD

Figure 2:
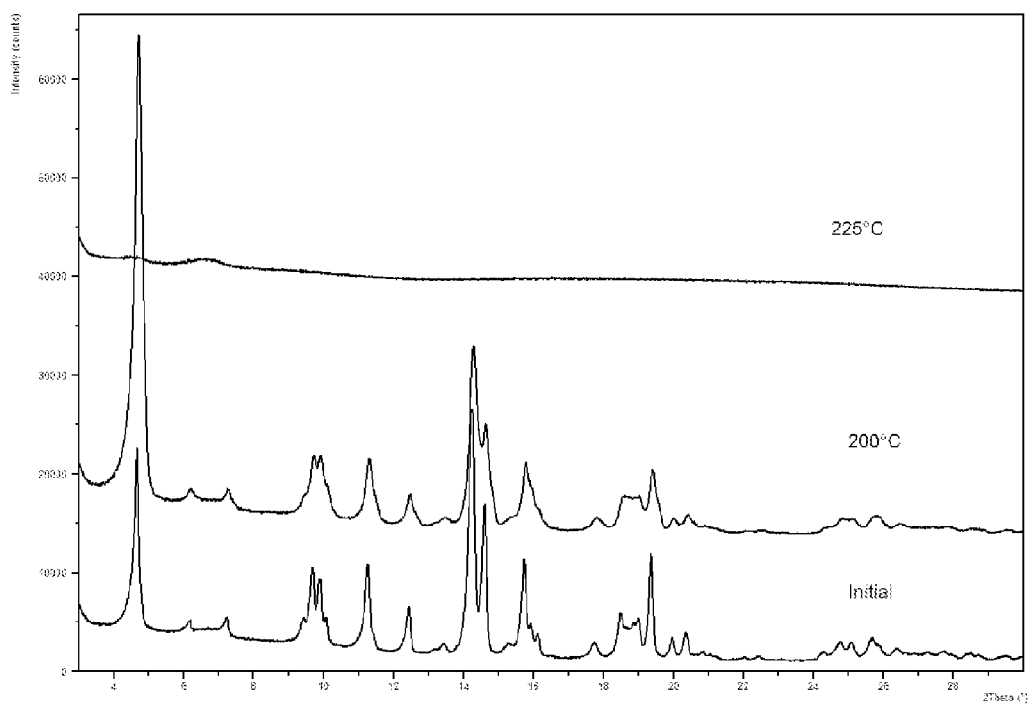
FIG. 2 illustrates the variable temperature XRPD patterns of Form $A_o$ (25° C.-225° C.).

Slow scans were measured after heating to the requested temperature and cooling back to 25° C. The initial scan matches the pattern for the Form $A_0$. After heating to 200° C., there are changes in intensity, but not in peak positions (FIG. 2). After heating to 255° C., the XRPD pattern is featureless and the sample on the VT plate was a golden hued solid in the shape of a droplet. All measurements were made with a flow of nitrogen gas through the sample stage.

Characterization of Form $A_0$ by Thermal Analysis

Figure 3:
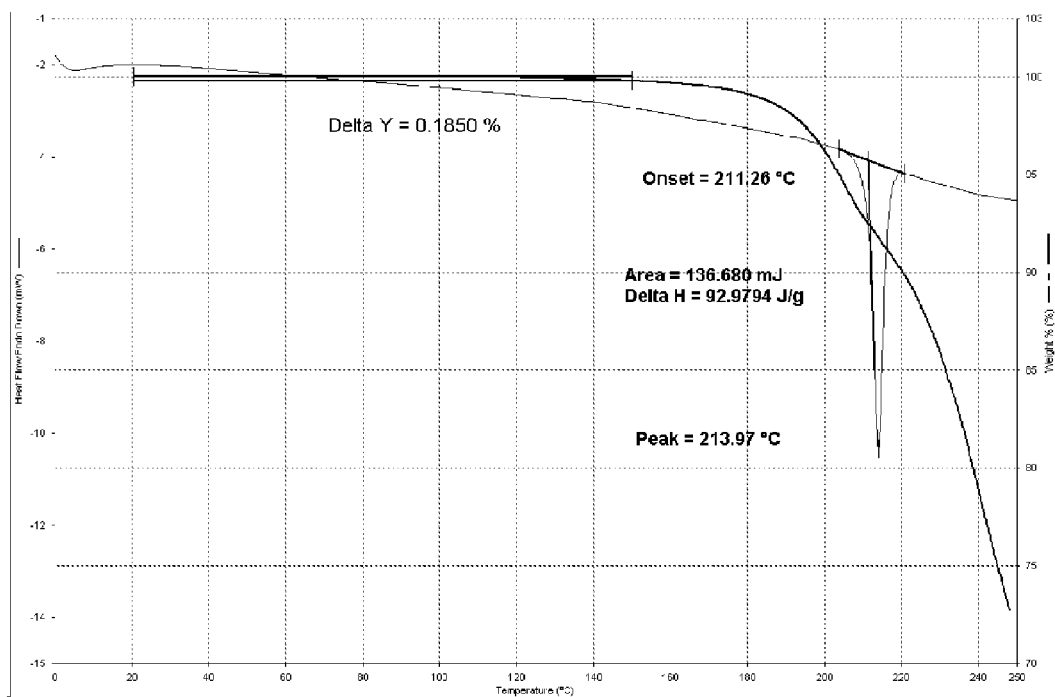
FIG. 3 illustrates the overlay of DSC and TGA curves of Form $A_o$.

Form $A_0$ shows a single peak at ca. 214.0° C. with an ΔHFus of 93.0 J/g. No loss of mass was detected by TGA. The existence of a desolvation process was discounted because a minimal loss of weight was detected by TGA (FIG. 3).

Characterization by Water Sorption of Form $A_0$ (Dm/Dt Mode)

Figure 4:
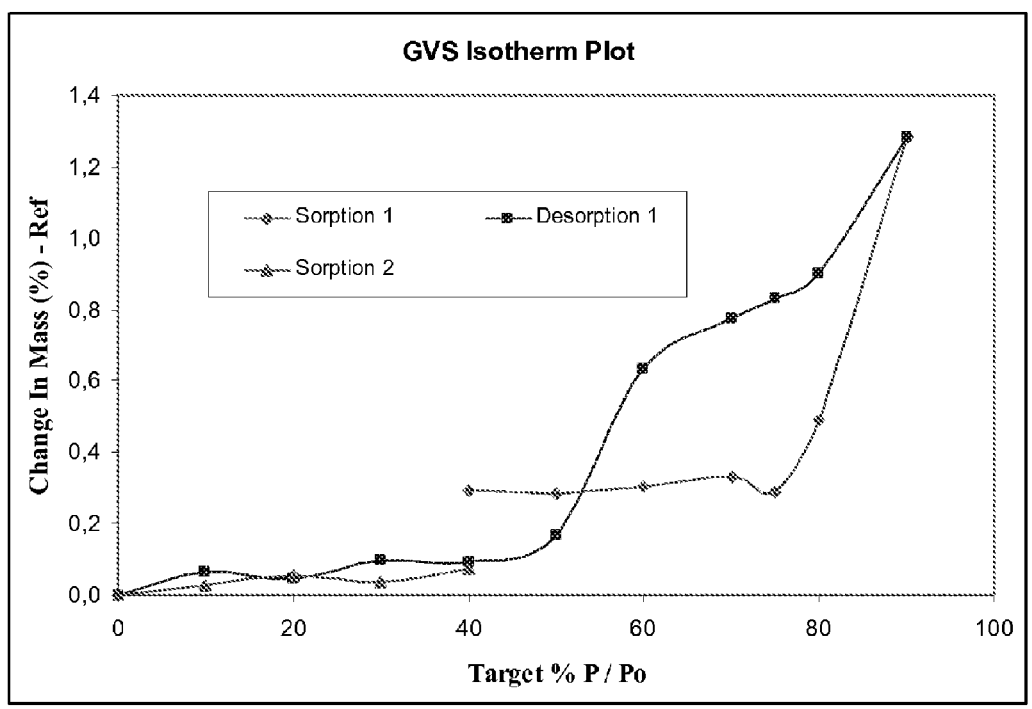
FIG. 4 illustrates the gravimetric vapor sorption isotherm of Form $A_o$.
Figure 5:
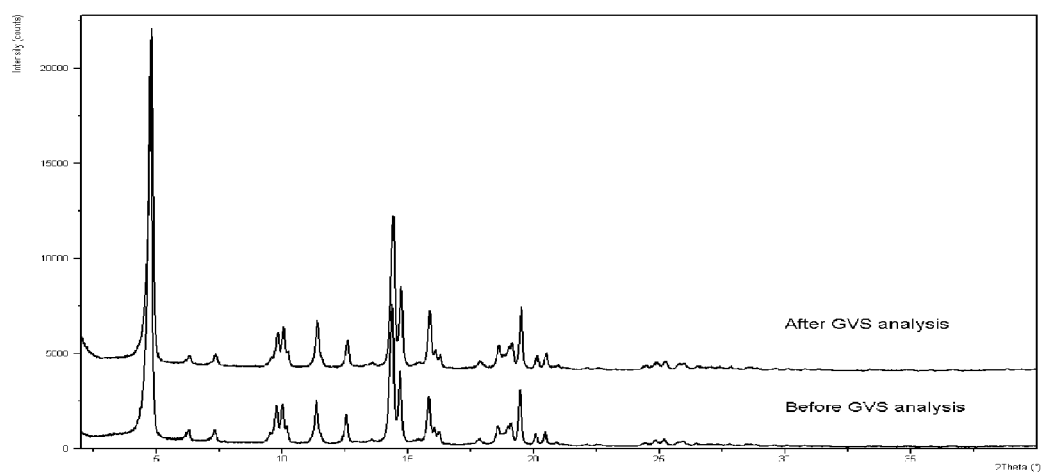
FIG. 5 illustrates the XRPD patterns of Form $A_o$ before and after GVS analysis.

Form $A_0$ from 40 to about 90% RH has a moisture uptake of less than 1.3% (w/w). In the second sorption step, the sample experienced a slow uptake of water (FIG. 4). XRPD analysis was performed on the sample after two cycles of the GVS experiment. The XRPD pattern of this material compares nicely to the pattern of the material before GVS (FIG. 5).

Characterization by FTIR Spectroscopy

Figure 6:
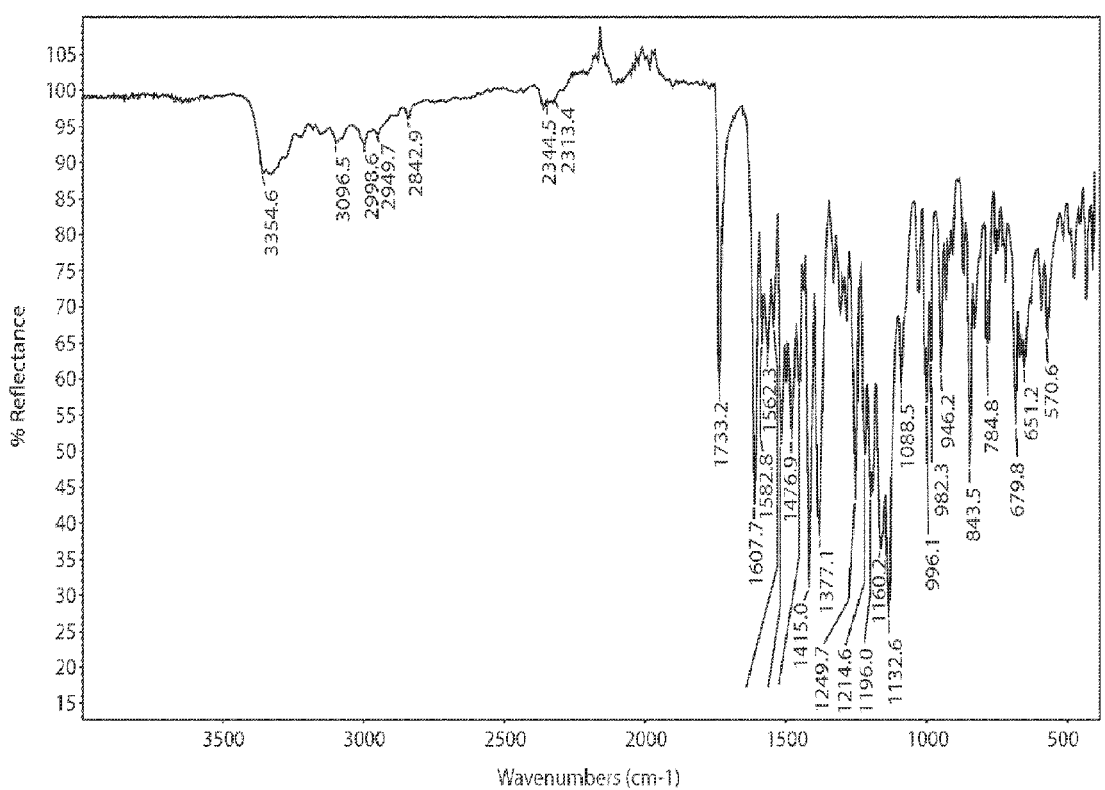
FIG. 6 illustrates the infrared spectra of Form $A_o$.

The Fourier transform infrared spectrum of Form Ao and its characteristic bands are provided in Table 16 and FIG. 6.

TABLE 16

Fourier Transform Infrared Bands Of Form $A_0$

| Infrared Frequency, $cm^{-1}$ | Assignment |
|---|---|
| 3359.1 | NH stretch PH—NH—R |
| 3096.5.0 | Aromatic CH stretch |
| 2940.8 | R—CH3 asym stretch |
| 2838.5 | R2—NH2+ stretch |
| 1733.3 | C = 0 stretch urea |
| 1607.3 | NH2 def Amide II |
| 1562.1 | Aromatic |
| 1414.8 | C—N stretch Amide |
| 1249.5 | Ph—O—C ether, asym stretch |
| 1132.5 | CH2—O—CH2 ether, asym stretch |
| 1088.4 | Ph—O—C ether, sym stretch |
| 826.2 | Ph—O—C ether, sym stretch |
| 679.7 | C—H rocking |

Optical Microscopy

Figure 7:
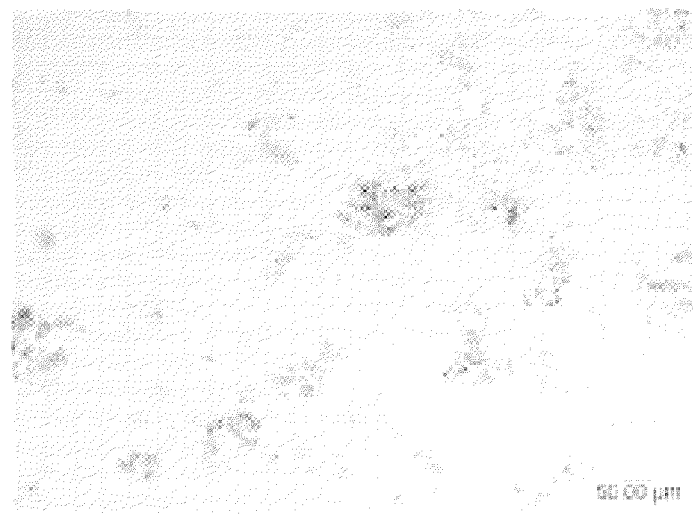
FIG. 7 is a photograph of Form $A_o$ at room temperature.

The sample of Form Ao showed small needles (magnification 100×) and the material exhibited birefringence (FIG. 7).

Bromide Form A1

Preparation

Crystallization by Maturation

Approximately 1.05 equivalents of the calculated quantity of hydrobromic acid (48%) to react with 80 mg of free base are weighed into a glass vial in 40000 μL of THF. The sample was heated from 20° C. to 80° C. at a rate of 5°

C./min and after 60 minutes cooled at a slow rate (0.25° C./min) to a final temperature of 5° C. and kept at that temperature for 18 hours using the HEL Polyblock™ Unit. The crystallization experiment was carried out in a glass vial (4.0 mL; 46×14.5 mm). The solid material was isolated by filtration and dried at 40° C. for 18 hours under house vacuum. The sample was analyzed by XRPD, DSC, TGA, FTIR, and OM.

Characterization by XRPD

Figure 8:
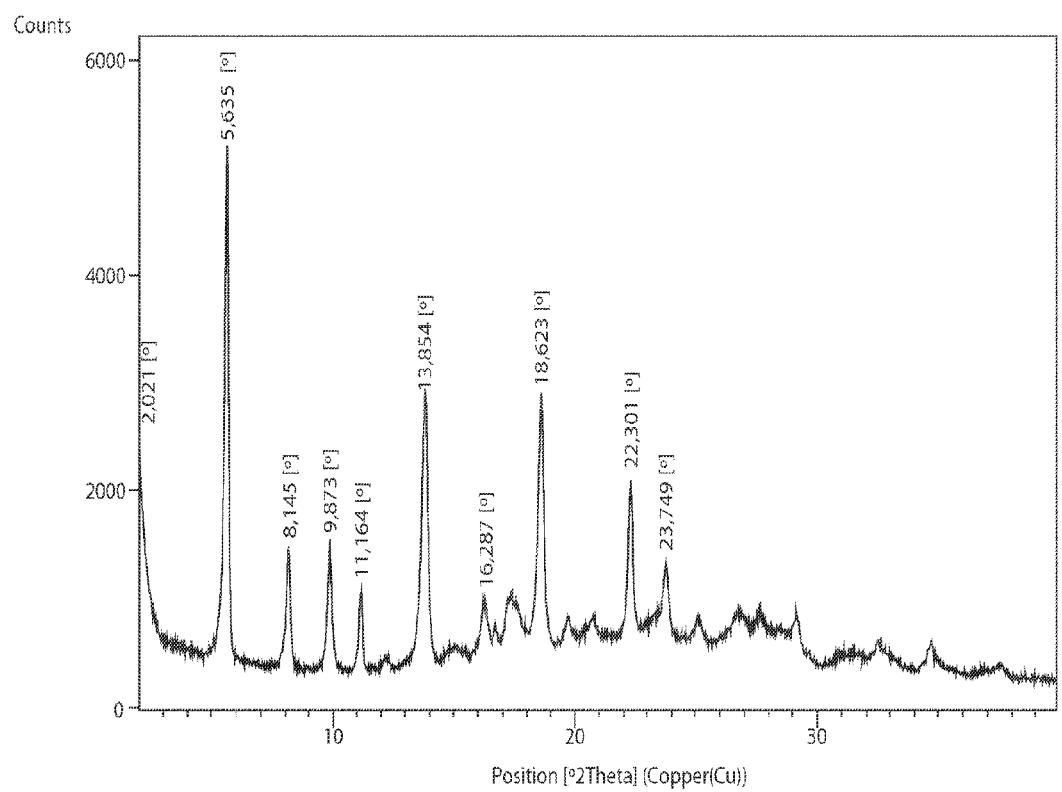
FIG. 8 illustrates the XRPD pattern of bromide Form $A_1$.

The peaks and X-ray diffraction pattern characteristic of the crystalline bromide Form A1 are shown in Table 17 and FIG. 8.

TABLE 17

Select Two Theta Positions (2θ). D-Spacings (D) And Relative Intensities (I) Of XRPD

| No. | Pos. [°2Th.] | d-spacing [Å] | Rel. Int. [%] |
|---|---|---|---|
| 1 | 2.02 | 43.68 | 10 |
| 2 | 5.64 | 15.67 | 100 |
| 3 | 8.15 | 10.85 | 23 |
| 4 | 9.87 | 8.95 | 24 |
| 5 | 11.16 | 7.92 | 15 |
| 6 | 13.85 | 6.39 | 51 |
| 7 | 16.29 | 5.44 | 9 |
| 8 | 17.15 | 5.17 | 6 |
| 9 | 18.62 | 4.76 | 49 |
| 10 | 19.68 | 4.51 | 5 |
| 11 | 22.30 | 3.98 | 31 |
| 12 | 23.75 | 3.74 | 14 |
| 13 | 27.66 | 3.22 | 5 |
| 14 | 29.18 | 3.06 | 7 |
| 15 | 34.75 | 2.58 | 5 |

Characterization of Bromide Form Ai by Thermal Analysis

Figure 9:
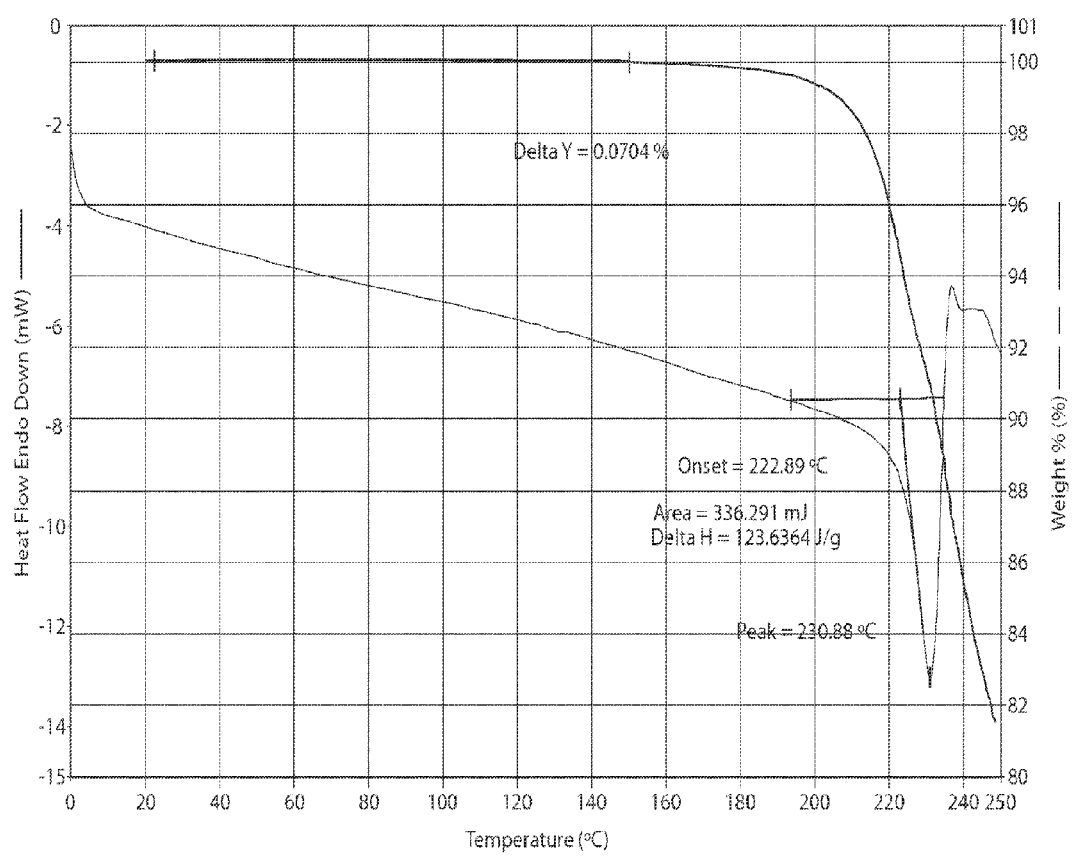
FIG. 9 illustrates the overlay of DSC and TGA curves of bromide Form $A_1$.

Bromide Form A1 shows a single peak at ca. 230.9° C. with an enthalpy of fusion (ΔHFus) of 123.6 J/g. Bromide Form A1 when studied by TGA demonstrated an average weight loss of 0.07% between 25° C. and 150° C. (FIG. 9).

Characterization by Water Sorption of Bromide Form Ai at 25° C. (Dm/Dt Mode)

Figure 10:
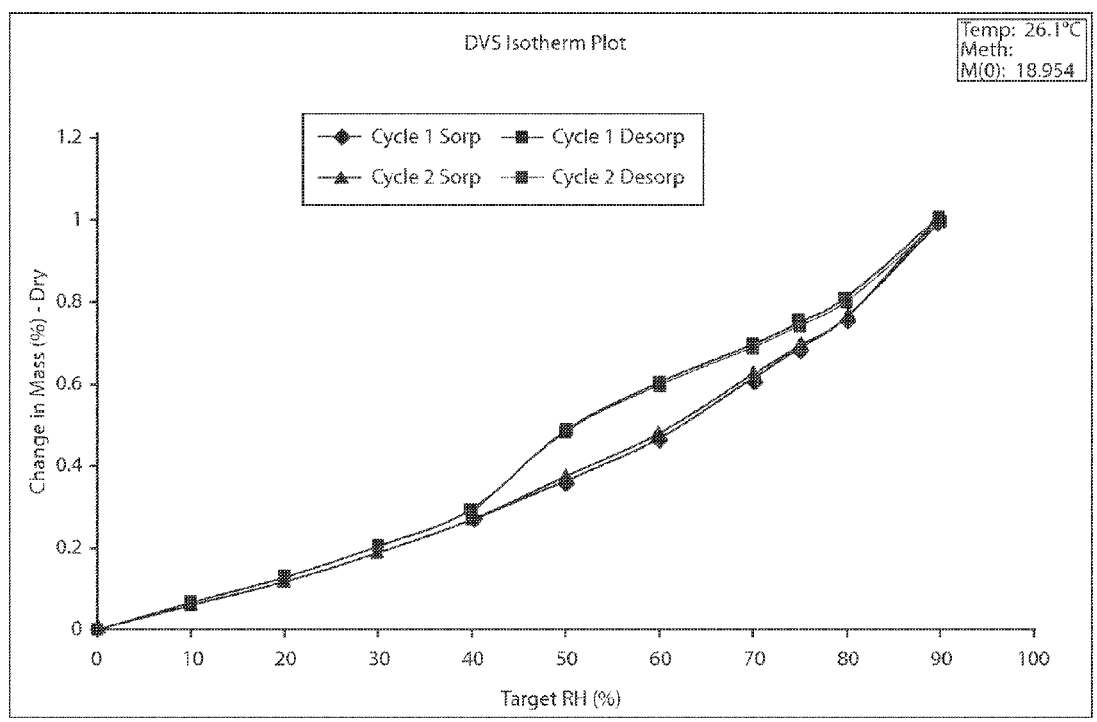
FIG. 10 illustrates the GVS isotherm of bromide Form $A_1$.
Figure 11:
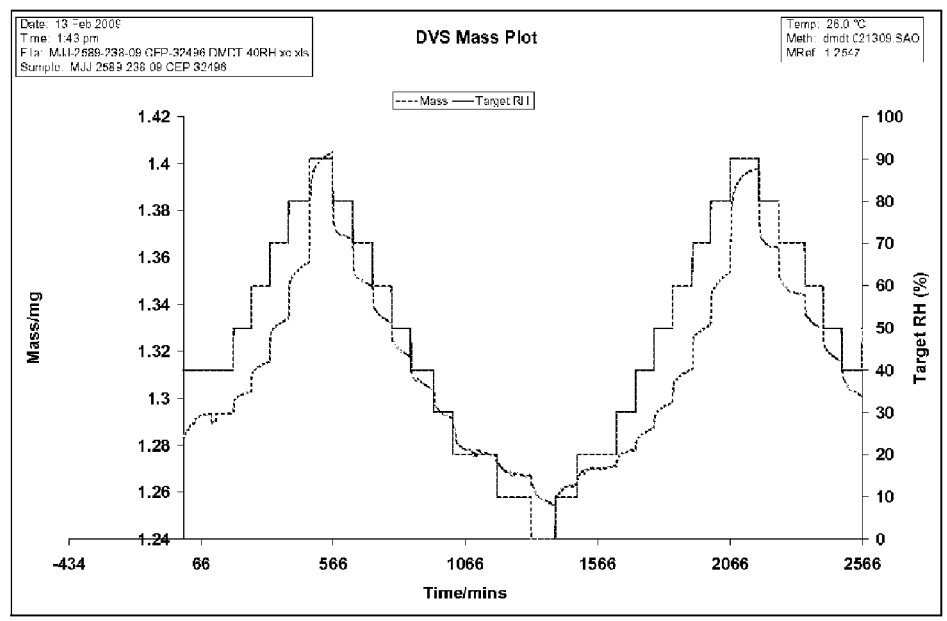
FIG. 11 illustrates the kinetic data/mass plot of bromide Form $A_1$.
Figure 12:
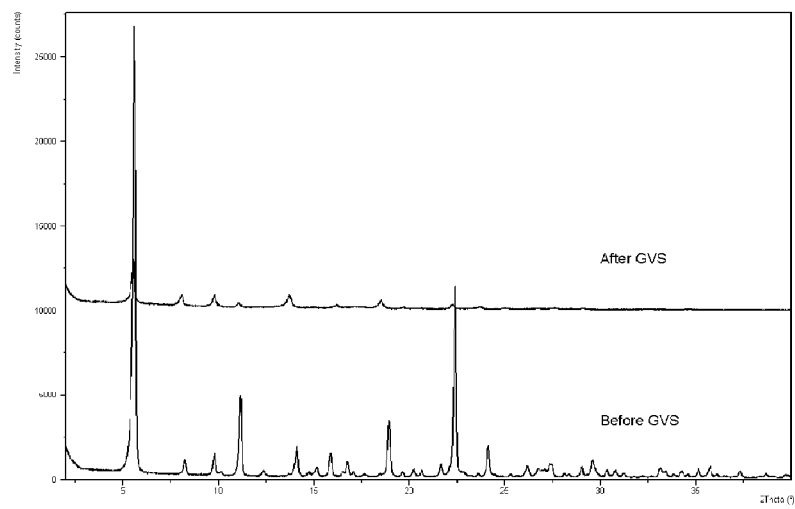
FIG. 12 illustrates the XRPD patterns of bromide Form $A_1$ before and after GVS analysis.

The amount of moisture adsorbed at 75% RH was less than 0.7% and approximately 1% at 90% RH. The adsorption and desorption curves overlap suggesting that Form A1 is not hygroscopic (FIG. 10 and FIG. 11). XRPD analysis was performed on the sample after the two cycle Gravimetric Vapor Sorption experiment. The XRPD pattern of this material compares nicely to the pattern of the material before GVS (FIG. 12).

Characterization by FTIR Spectroscopy

Figure 13:
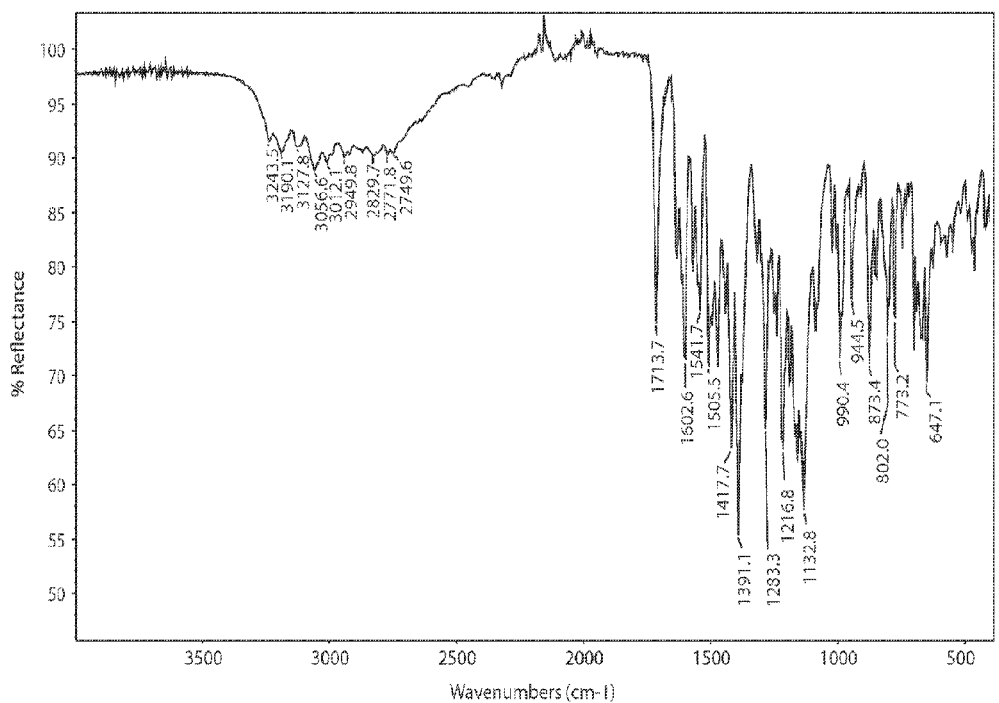
FIG. 13 illustrates the FTIR spectra of bromide Form $A_1$.

The Fourier transform infrared spectrum of bromide Form A1 and its characteristic bands are provided in Table 18 and FIG. 13.

TABLE 18

FTIR Bands Of Bromide Form $A_1$

| Infrared Frequency, cm−1 | Assignment |
|---|---|
| 3243.5 | NH stretch Ph—NH—R |
| 3056.6 | Aromatic CH stretch |
| 2949.8 | R—$CH_3$ asym stretch |
| 2749.6 | CH stretch |
| 1713.7 | C═O stretch Urea |
| 1632.4 | $NH_2$ def Amide II |
| 1602.6 | $R_2$—$NH_2^+$ def |
| 1417.7 | C—N stretch Amide |
| 1216.8 | Ph—O—C ether, asym stretch |
| 1132.8 | $CH_2$—O—$CH_2$ ether, asym stretch |
| 1065.4 | Ph—O—C ether, sym stretch |

TABLE 18-continued

FTIR Bands Of Bromide Form $A_1$

| Infrared Frequency, cm−1 | Assignment |
|---|---|
| 873.4 | Ph—O—C ether, sym stretch |
| 647.1 | CH rock |

Optical Microscopy

The sample of bromide Form Ai showed aggregates and small needles (magnified 100×). The material exhibited birefringence (FIG. 14).

Chloride Form Ai

Preparation

Crystallization

The chloride Form A1 was formed by dissolving the Form Ao in tetrahydrofuran/isopropyl acetate. After the addition of 1.3 equivalents of 5-6N hydrogen chloride in isopropanol, the mixture was stirred overnight. The isolated yield was 96.6%. The sample was analyzed by XRPD, DSC, TGA, FTIR, and OM.

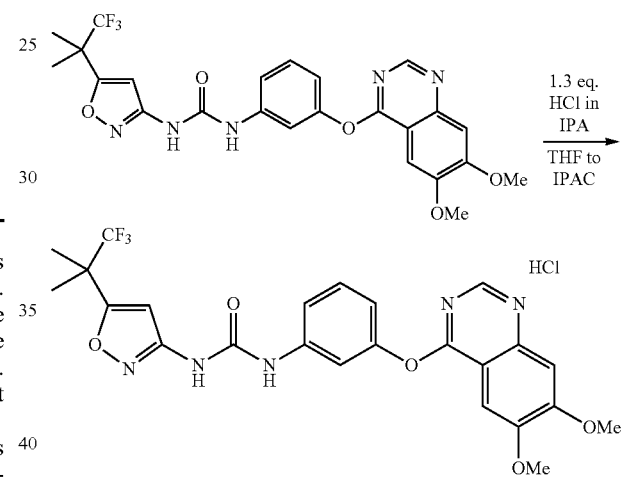

Characterization by XRPD

The peaks and X-ray diffraction pattern characteristic of the crystalline chloride Form $A_1$ are shown in Table 19 and FIG. 15.

TABLE 19

Select Two Theta Positions (2θ). D-Spacings (d) And Relative Intensities (I) Of XRPD

| No. | Pos. [°2Th.] | d-spacing [Å] | Rel. Int. [%] |
|---|---|---|---|
| 1 | 5.67 | 15.59 | 100 |
| 2 | 8.55 | 10.34 | 29 |
| 3 | 9.96 | 8.87 | 26 |
| 4 | 10.46 | 8.45 | 19 |
| 5 | 11.24 | 7.87 | 8 |
| 6 | 12.30 | 7.19 | 12 |
| 7 | 14.10 | 6.28 | 16 |
| 8 | 14.48 | 6.11 | 83 |
| 9 | 14.81 | 5.98 | 22 |
| 10 | 15.35 | 5.77 | 22 |
| 11 | 15.89 | 5.57 | 44 |
| 12 | 17.08 | 5.19 | 15 |
| 13 | 17.37 | 5.10 | 10 |
| 14 | 17.73 | 5.00 | 15 |
| 15 | 19.36 | 4.58 | 27 |

TABLE 19-continued

Select Two Theta Positions (2θ). D-Spacings (d) And Relative Intensities (I) Of XRPD

| No. | Pos. [°2Th.] | d-spacing [Å] | Rel. Int. [%] |
|---|---|---|---|
| 16 | 20.96 | 4.24 | 13 |
| 17 | 21.48 | 4.13 | 11 |
| 18 | 21.66 | 4.10 | 8 |
| 19 | 22.50 | 3.95 | 67 |
| 20 | 22.87 | 3.89 | 8 |
| 21 | 22.98 | 3.87 | 6 |
| 22 | 24.08 | 3.69 | 8 |
| 23 | 24.57 | 3.62 | 8 |
| 24 | 26.03 | 3.42 | 5 |
| 25 | 26.23 | 3.39 | 5 |
| 26 | 26.83 | 3.32 | 23 |
| 27 | 27.56 | 3.23 | 25 |
| 28 | 29.07 | 3.07 | 8 |
| 29 | 29.99 | 2.98 | 15 |
| 30 | 20.96 | 4.24 | 13 |

The highest peak (intensity 100%) is set in bold letters.

Characterization by VT-XRPD

No solid-solid transformation takes place m the between 25° C. and 200° C. for Chloride Form $A_1$. Upon heating to 245° C., the sample melts with no indication of recrystallization on cooling to 25° C. (FIG. 16).

Characterization of Chloride Form Ai by Thermal Analysis

The chloride Form A1 shows a single peak at ca. 236.1° C. with an ΔHFus of 256.1 J/g. TGA measurement demonstrated an average weight loss of 0.2% between 25° C. and 150° C. (FIG. 17).

Characterization by Water Sorption of Chloride Form Ai at 25° C. (Dm/Dt Mode)

The first adsorption curve (FIG. 18) exhibits a weight increase of 1.7% through 90% RH. The second cycle for Form A1 closely reproduces the first cycle. No form change occurred during the GVS cycles. The sample was the same crystalline form after the GVS experiment as shown by the XRPD patterns in FIG. 19.

Characterization of Chloride Form $A_1$ by FTIR

The FTIR spectrum for Form A1 is shown in FIG. 20, and the proposed peak assignments are given in Table 20.

TABLE 20

FTIR Bands For Chloride Form $A_1$

| Infrared Frequency, cm$^{-1}$ | Assignment |
|---|---|
| 3199.0 | NH stretch; Urea |
| 3061.1 | CH stretch; m-distributed aromatic |
| 3007.7 | CH stretch; 1,2,4,5-substituted aromatic |
| 2940.9 | R—CH$_3$ asym stretch |
| 2709.5 | NH stretch; aromatic NH$^+$ |
| 1711.2 | C═O stretch; Urea |
| 1632.6 | Aromatic ring stretch |
| 1602.9 | Aromatic ring stretch |
| 1541.9 | NH def Urea |
| 1499.6 | Aromatic ring stretch |
| 1391.1 | N—C—N stretch Urea |
| 1283.4 | Ph—O—C ether, asym stretch |
| 1133.1 | C—F stretch |
| 1029.5 | Ph—O—C ether, sym stretch |
| 885.2 | Ph—O—C ether, sym stretch |
| 803.3 | Aromatic ring def |
| 700.5 | Aromatic ring bend |

Optical Microscopy

The sample of chloride Form $A_1$ showed aggregates and small needles (magnified 100×). The material exhibited birefringence (FIG. 21).

Malonate Form $A_1$

Preparation

Crystallization by Maturation

Approximately 1.05 equivalents of the calculated quantity of malonic acid to react with 80 mg of Form Ao were weighed into a glass vial with 4000 μL of THF. This mixture was slurried for a total of 48 hours with alternating 4 hour periods at 50° C. and 5° C. (±0.5° C./min) using the HEL Polyblock™ Unit. The crystallization experiments were carried out in glass vials (4.0 mL. 346×14.5 mm). The solid material was isolated by filtration and dried at 40° C. for 18 hours under house vacuum. The sample was analyzed by XRPD, DSC, TGA, GVS, FTIR, and OM.

Characterization by XRPD

The peaks and X-ray diffraction pattern characteristic of the crystalline malonate Form A1 are shown in Table 21 and FIG. 22.

TABLE 21

Select Two Theta Positions (2θ). D-Spacings (d) And Relative Intensities (I) Of XRPD

| No. | Pos. [°2Th.] | d-spacing [Å] | Rel. Int. [%] |
|---|---|---|---|
| 1 | 3.57 | 24.72 | 100 |
| 2 | 3.66 | 24.12 | 72 |
| 3 | 5.97 | 14.80 | 6 |
| 4 | 7.08 | 12.48 | 26 |
| 5 | 7.18 | 12.31 | 11 |
| 6 | 10.16 | 8.70 | 7 |
| 7 | 10.44 | 8.46 | 40 |
| 8 | 10.59 | 8.34 | 32 |
| 9 | 11.05 | 8.00 | 14 |
| 10 | 12.16 | 7.27 | 5 |
| 11 | 12.89 | 6.86 | 8 |
| 12 | 14.12 | 6.27 | 29 |
| 13 | 15.30 | 5.79 | 8 |
| 14 | 16.20 | 5.47 | 6 |
| 15 | 16.64 | 5.32 | 6 |
| 16 | 17.36 | 5.10 | 7 |
| 17 | 17.67 | 5.01 | 47 |
| 8 | 21.21 | 4.18 | 20 |
| 19 | 22.32 | 3.98 | 6 |
| 20 | 25.73 | 3.46 | 12 |
| 21 | 26.03 | 3.42 | 38 |
| 22 | 26.30 | 3.39 | 19 |
| 23 | 26.93 | 3.31 | 36 |
| 24 | 27.64 | 3.22 | 5 |
| 25 | 28.03 | 3.18 | 15 |
| 26 | 28.42 | 3.14 | 6 |

The highest peak (intensity 100%) is set in bold letters.

Characterization of Malonate Form A1 by Thermal Analysis

Malonate Form $A_1$ gave a single peak at ca. 171.7° C. with an ΔHfus of 140.6 J/g. Malonate Form $A_1$ when studied by TGA demonstrated an average weight loss of 1.7% between 25° C. and 150° C. (FIG. 23).

Characterization by Water Sorption of Malonate Form $A_1$ at 25° C. (Dm/Dt Mode)

There is a steady uptake in water over the RH range of 0-90%. Surface adsorption with limited bulk absorption is occurring. The total uptake is <4%. No form change occurred during the GVS cycles.

Characterization by Water Sorption of Malonate Form A1 at 25° C. (Dm/Dt Mode)

The FTIR spectrum for malonate Form A1 is shown in FIG. 24, and the proposed peak assignments are given in Table 22.

TABLE 22

FTIR Bands For Malonate Form $A_1$

| Infrared Frequency, cm$^{-1}$ | Assignment |
| --- | --- |
| 3136.7 | NH stretch; Urea |
| 3061.1 | CH stretch; m-distributed aromatic |
| 3007.7 | CH stretch; 1,2,4,5-substituted aromatic |
| 2936.5 | R—CH$_3$ asym stretch |
| 2825.5 | NH stretch; aromatic NH$^+$ |
| 1708.3 | C═O stretch; Urea |
| 1632.6 | Aromatic ring stretch |
| 1608.1 | Aromatic ring stretch |
| 1575.4 | NH def Urea |
| 1515.1 | Aromatic ring stretch |
| 1398.4 | N—C—N stretch Urea |
| 1283.2 | Ph—O—C ether, asym stretch |
| 1131.8 | C—F stretch |
| 1088.7 | Ph—O—C ether, sym stretch |
| 993.7 | Ph—O—C ether, sym stretch |
| 821.9 | Aromatic ring def |
| 733.6 | Aromatic ring bend |

Optical Microscopy

The sample of malonate Form $A_1$ showed aggregates (magnified 100×) and the material exhibited birefringence (FIG. 25).

Phosphate Form Ai

Preparation

Crystallization by Maturation

Approximately 1.05 equivalents of the calculated quantity of ortho-phosphoric acid to react with 80 mg of Form Ao were added to a glass vial with 2 mL of acetone. This mixture was slurried for a total of 48 hours with alternating 4 hour periods at 50° C. and 5° C. (±0.5° C./min) using the HEL Polyblock™ Unit. The crystallization experiments were carried out in glass vials (40 mL. 46×14.5 mm). The solid material was isolated by filtration and dried at 40° C. for 18 hours under house vacuum. The sample was analyzed by XRPD, DSC, TGA, GVS, FTIR, and OM.

Characterization by XRPD

The peaks and X-ray diffraction pattern characteristic of the crystalline phosphate Form A1 are shown in Table 23 and FIG. 26.

TABLE 23

Select Two Theta Positions (2θ). D-Spacings (i) And Relative Intensities (I) Of XRPD

| No. | Pos. [2θ.] | d-spacing [Å] | Rel. Int. [%] |
| --- | --- | --- | --- |
| 1 | 3.26 | 27.11 | 22 |
| 2 | 6.47 | 13.66 | 100 |
| 3 | 9.63 | 9.18 | 19 |
| 4 | 11.55 | 7.66 | 5 |
| 5 | 12.89 | 6.86 | 24 |
| 6 | 15.54 | 5.70 | 38 |
| 7 | 16.09 | 5.50 | 15 |
| 8 | 18.49 | 4.79 | 6 |
| 9 | 21.55 | 4.12 | 7 |

The highest peak (intensity 100%) is set in bold letters.

Characterization of Phosphate Form $A_1$ by Thermal Analysis

Phosphate Form $A_1$ shows a single peak at ca. 186.3° C. with an enthalpy of fusion (ΔHFus) of 78.7 J/g (FIG. 27). Phosphate Form $A_1$ when studied by TGA demonstrated an average weight loss of 0.12% between 25° C. and 150° C.

Characterization by Water Sorption of Phosphate Form Ai at 25° C. (Dm/Dt Mode)

Figure 30:
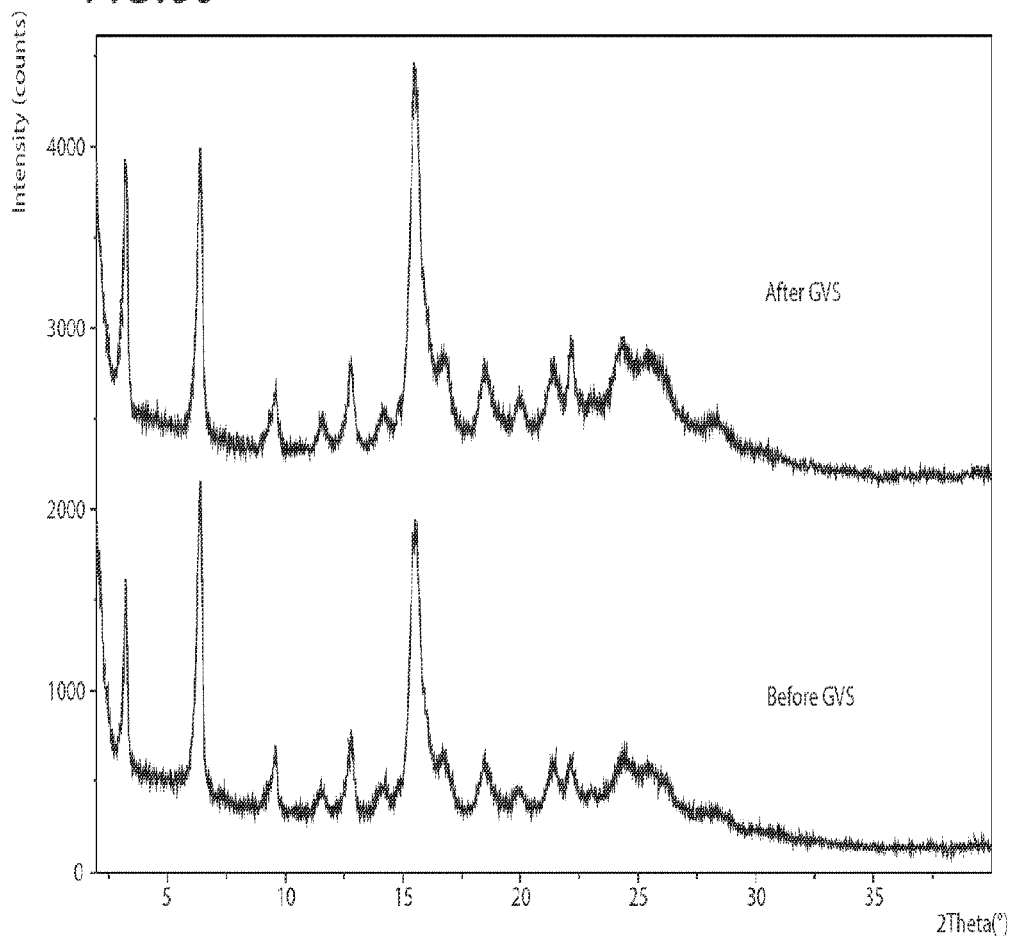
FIG. 30 illustrates the XRPD patterns of phosphate Form $A_1$ before and after GVS analysis.

The amount of moisture adsorbed at 75% RH was less than 1.8% and approximately 2.7% at 90% RH. The adsorption and desorption curves overlap suggesting that Compound I phosphate Form A1 is not hygroscopic (FIG. 28 and FIG. 29). XRPD analysis was performed on the sample after the two cycles of the GVS experiment. The XRPD pattern of this material compares nicely to the pattern of the material before GVS (FIG. 30).

Characterization of Phosphate Form $A_1$ by FTIR

The FTIR spectrum for phosphate Form A1 is shown m FIG. 31, and the proposed peak assignments are given in Table 24.

TABLE 24

FTIR Bands For Phosphate Form $A_1$

| Infrared Frequency, cm$^{-1}$ | Assignment |
| --- | --- |
| 3288.0 | NH stretch; Urea |
| 3216.8 | CH stretch; m-distributed aromatic |
| 3087.8 | CH stretch; 1,2,4,5-substituted aromatic |
| 2927.6 | R—CH$_3$ asym stretch |
| 2838.6 | NH stretch; aromatic NH$^+$ |
| 1726.1 | C═O stretch; Urea |
| 1641.5 | Aromatic ring stretch |
| 1613.0 | Aromatic ring stretch |
| 1510.0 | NH def Urea |
| 1494.2 | Aromatic ring stretch |
| 1421.2 | N—C—N stretch Urea |
| 1285.4 | Ph—O—C ether, asym stretch |
| 1133.5 | C—F stretch |
| 1002.3 | Ph—O—C ether, sym stretch |
| 984.0 | Ph—O—C ether, sym stretch |
| 861.6 | Aromatic ring def |

Optical Microscopy

The sample of Phosphate Form A1 showed aggregate and small particles (magnified 100×). The material exhibited birefringence (FIG. 32).

Kinetic Solubility Measurement

Solubility measurements of Compound I free base, Form Ao, and four salts were performed in pure water.

Sample Solution Preparation

The free base and the salts listed in the table below were added in excess (saturation) to water in a 2.0 mL glass vial. The samples were put on an end-to-end rotator (50 rpm) at ambient room temperature up to 20 minutes. After 20 minutes, a sampling was taken for HPLC analysis.

The results are presented in Table 25. The aqueous solubility measurement confirmed the chloride salt was the best salt for dissolution in pure water (pH=7).

TABLE 25

Aqueous Solubility Measurement Of The Free Base And The Salts

| Material tested | mg/mL | pH |
| --- | --- | --- |
| Free base $A_0$ | <0.01 | 7.4 |
| Bromide $A_1$ | 0.1 | 6.6 |
| Chloride $A_1$ | 0.56 | 7.3 |
| Malonate $A_1$ | 0.07 | 6.6 |
| Phosphate $A_1$ | 0.09 | 6.8 |

The amount of compound dissolved in water is expressed as free base.

Relationship Between Solid State Forms

Solid State Stress Stability

Stress stability studies were performed to get a timely impression of the influence of temperature and humidity on Form stability.

Form $A_0$ and Chloride Form $A_1$

In the solid state at standard ICH stressed conditions of 40° C./75% relative humidity without desiccant, free base Form Ao and chloride Form A1 were stable for 28 days (Table 26 and Table 27).

TABLE 26

Stability Data For Form $A_0$ At 40° C./75% RH

| Sample ID | Time/ days | XRPD | DSC (°) | TGA (%*) | HPLC Assay (%) | Area Purity (%) |
|---|---|---|---|---|---|---|
| 248-0 | 0 | Form $A_0$ | 214.0 | 1.8 | 100.0 | 98.3 |
| 248-6 | 6 | Form $A_0$ | 215.4 | 0.2 | 102.3 | 98.5 |
| 248-14 | 14 | Form $A_0$ | 215.5 | 0.2 | 100.5 | 98.5 |
| 248-28 | 28 | Form $A_0$ | 215.7 | 0.01 | 102.4 | 98.2 |

*weight loss 25° C. to 150° C.

TABLE 27

Stability Data For Chloride Form $A_1$ At 40° C./75% RH

| Sample ID | Time/ days | XRPD | DSC (°) | TGA (%*) | HPLC Assay (%) | Area Purity (%) |
|---|---|---|---|---|---|---|
| 274-0 | 0 | Form $A_1$ | 228.9 | 0.8 | 99.9 | 99.5 |
| 274-7 | 7 | Form $A_1$ | 224.7 | 0.1 | 98.3 | 98.7 |
| 274-14 | 14 | Form $A_1$ | 229.2 | 0.1 | 98.7 | 97.6 |
| 274-8 | 28 | Form $A_1$ | 228.5 | 0.3 | 100.4 | 96.4 |

*weight loss 25° C. to 150° C.

The invention claimed is:

1. A crystalline form of N-[3-[(6,7-dimethoxy-4-quinazolinyl)oxy]phenyl]-N'-[5-(2,2,2-trifluoro-1,1-dimethylethyl)-3-isoxazolyl]-urea, wherein said crystalline form is characterized by an x-ray powder diffraction pattern comprising a peak at a 2-theta value of about 4.8±0.2 degrees.

2. The crystalline form according to claim 1, wherein said x-ray powder diffraction pattern further comprises a peak at a 2-theta value of about 14.4±0.2 degrees.

3. The crystalline form according to claim 2, wherein said x-ray powder diffraction pattern further comprises a peak at a 2-theta value of about 14.3±0.2 degrees.

4. The crystalline form according to claim 3, wherein said x-ray powder diffraction pattern further comprises a peak at a 2-theta value of about 14.7±0.2 degrees.

5. The crystalline form according to claim 1, wherein said x-ray powder diffraction pattern further comprises a peak at a 2-theta value of about 14.4±0.2 degrees, about 14.3±0.2 degrees, and about 14.7±0.2 degrees.

6. The crystalline form according to claim 1, wherein said crystalline form is further characterized by exhibiting a peak in a differential scanning calorimetry scan of about 214° C.

7. The crystalline form according to claim 5, wherein said crystalline form is further characterized by exhibiting a peak in a differential scanning calorimetry scan of about 214° C.

8. The crystalline form according to claim 1, wherein said crystalline form is further characterized by exhibiting a moisture uptake of less than about 1.3% by weight in conditions of relative humidity from about 40% to about 90%.

9. The crystalline form according to claim 1, wherein said crystalline form is further characterized by exhibiting Fourier transform infrared spectrum bands at frequencies of about 3359.1 $cm^{-1}$, about 1733.3 $cm^{-1}$, about 1607.3 $cm^{-1}$, and about 1414.8 $cm^{-1}$.

10. The crystalline form according to claim 1, wherein said crystalline form is further characterized by exhibiting a peak in a differential scanning calorimetry scan of about 214° C., and by exhibiting Fourier transform infrared spectrum bands at frequencies of about 3359.1 $cm^{-1}$, about 1733.3 $cm^{-1}$, about 1607.3 $cm^{-1}$, and about 1414.8 $cm^{-1}$.

11. A pharmaceutical composition comprising a crystalline form of N-[3-[(6,7-dimethoxy-4-quinazolinyl)oxy]phenyl]-N'-[5-(2,2,2-trifluoro-1,1-dimethylethyl)-3-isoxazolyl]-urea and a pharmaceutically acceptable excipient, wherein said crystalline form is characterized by an x-ray powder diffraction pattern comprising a peak at a 2-theta value of about 4.8±0.2 degrees.

12. The pharmaceutical composition according to claim 11, wherein said composition is in a form suitable for oral administration to a subject.

13. The pharmaceutical composition according to claim 12, wherein said composition is in the form of a tablet, pill, powder, capsule or troche.

14. The pharmaceutical composition according to claim 13, wherein said composition is in the form of a tablet, pill, or capsule.

15. The pharmaceutical composition according to claim 11, wherein said composition comprises between about 1 mg to about 500 mg of N-[3-[(6,7-dimethoxy-4-quinazolinyl)oxy]phenyl]-N'-[5-(2,2,2-trifluoro-1,1-dimethylethyl)-3-isoxazolyl]-urea.

* * * * *